US 8,401,664 B2

(12) United States Patent
Chow et al.

(10) Patent No.: US 8,401,664 B2
(45) Date of Patent: Mar. 19, 2013

(54) SYSTEM AND METHOD FOR CHARGING A POWER CELL IN AN IMPLANTABLE MEDICAL DEVICE

(75) Inventors: Eric Y. Chow, Houston, TX (US); Anthony W. Cowley, Houston, TX (US); David L. Thompson, Houston, TX (US); Jianxiang Shen, Houston, TX (US); James L. Flesher, Charlotte, NC (US); Saadat Hussain, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 111 days.

(21) Appl. No.: 13/097,833

(22) Filed: Apr. 29, 2011

(65) Prior Publication Data

US 2012/0277829 A1 Nov. 1, 2012

(51) Int. Cl.
*A61N 1/00* (2006.01)
(52) U.S. Cl. ............................................ 607/61; 607/33
(58) Field of Classification Search .............. 607/27–33, 607/60, 61
See application file for complete search history.

(56) References Cited

U.S. PATENT DOCUMENTS

| 4,014,346 | A | 3/1977 | Brownlee et al. |
| 5,411,537 | A | 5/1995 | Munshi et al. |
| 5,690,693 | A | 11/1997 | Wang et al. |
| 5,702,431 | A | 12/1997 | Wang et al. |
| 5,713,939 | A | 2/1998 | Nedungadi et al. |
| 5,749,909 | A | 5/1998 | Schroeppel et al. |
| 2005/0119716 | A1 | 6/2005 | McClure et al. |
| 2007/0129767 | A1 | 6/2007 | Wahlstrand |
| 2010/0076524 | A1 | 3/2010 | Forsberg et al. |
| 2010/0106223 | A1 | 4/2010 | Grevious et al. |
| 2010/0114253 | A1 | 5/2010 | Wahlstrand |

FOREIGN PATENT DOCUMENTS

WO 2011022166 A1 2/2011

OTHER PUBLICATIONS

International Application No. PCT/US2011/063898, International Search Report And Written Opinion dated Jul. 3, 2012, 11 pages.

*Primary Examiner* — Scott Getzow
(74) *Attorney, Agent, or Firm* — Cyberonics, Inc.

(57) ABSTRACT

Apparatus and methods for charging a power cell in an implantable medical device ("IMD") are disclosed herein. In one embodiment, a method includes providing an electrical pulse to an inductor external to the IMD. A frequency of an oscillation signal induced in the inductor by the current pulse is measured. The inductor is driven with an oscillating signal having a frequency based on the measured frequency of the oscillation signal. The power cell is charged using current induced in the IMD by the driving of the inductor.

25 Claims, 13 Drawing Sheets

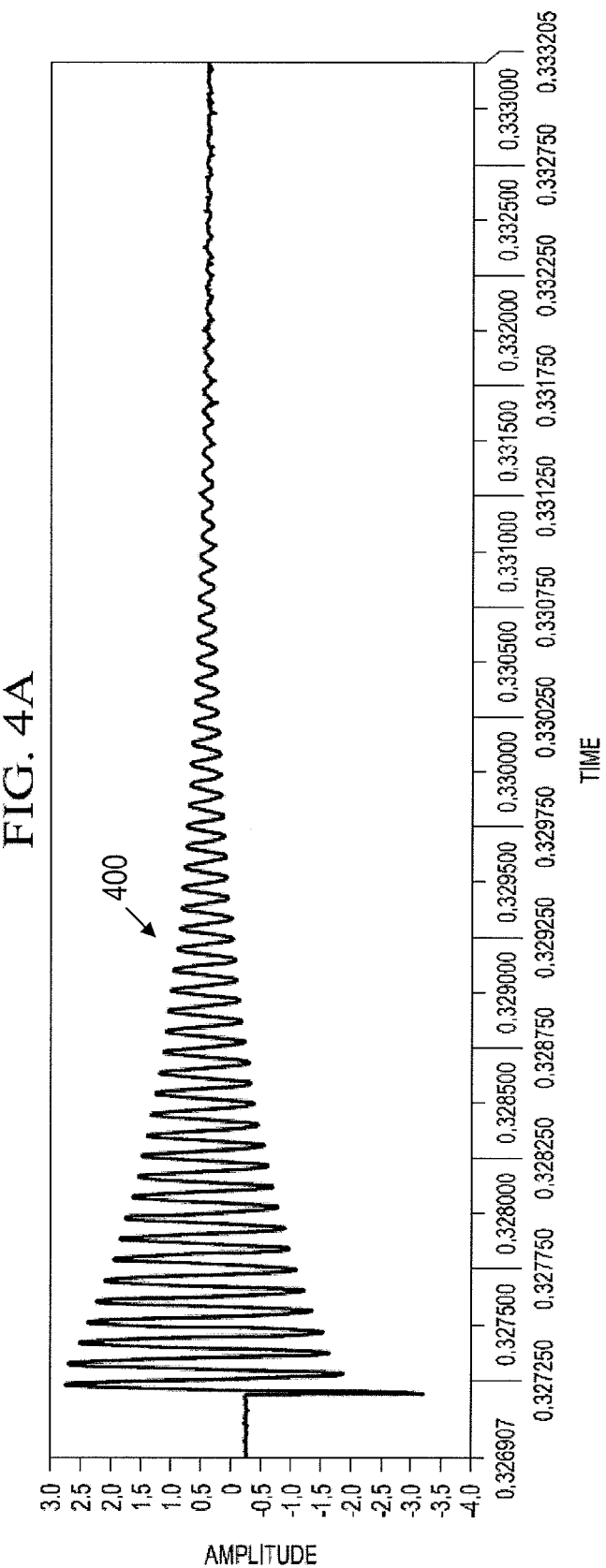

SYSTEM AND METHOD FOR CHARGING A POWER CELL IN AN IMPLANTABLE MEDICAL DEVICE

BACKGROUND

Medical treatments for disorders of the nervous system, such as seizure disorders (e.g., epilepsy), have improved in recent decades. One available treatment involves the application of an electrical signal to reduce various symptoms or effects caused by such neural disorders. For example, electrical signals have been successfully applied at strategic locations in the human body to provide various benefits, including a reduction of seizure occurrence and the improvement of other medical conditions. An example of such a treatment regimen involves the application of electrical stimulation to the vagus nerve of the human body to reduce or eliminate epileptic seizures, as described in U.S. Pat. No. 4,702,254, which is incorporated herein by reference.

Electrical stimulation of a target tissue of a patient's body (e.g., vagus nerve stimulation) may be provided by implanting an electrical device (known as an implantable medical device, or IMD) underneath the skin of a patient and electrically stimulating the target tissue. Vagus nerve stimulators, cardiac pacemakers, and cardioverter defibrillators are exemplary IMDs. Most IMDs are powered by a battery housed within the IMD. Both rechargeable and non-rechargeable batteries have been used in IMDs. When a non-rechargeable battery is used, the IMD must be surgically removed from a patient's body before the battery is completely exhausted so that a new device (or battery) may be installed. Unfortunately, accurate prediction of battery life can be difficult when the battery is discharged at an uncontrolled rate, e.g., when therapy is delivered on an "as needed" or patient controlled basis, and consequently IMD replacement scheduling is subject to error. Moreover, surgery is costly and inconvenient, and not without risk to the patient. Therefore, it is desirable to avoid or postpone surgery by providing an IMD with longer operational life. The operational life of an IMD may be extended by providing a rechargeable rather than a non-rechargeable battery in the IMD.

Furthermore, when using a non-rechargeable battery, the features and functionalities provided by an IMD are often limited to extend battery life. In order to provide an acceptable operational life without unduly increasing battery size (and consequently increasing IMD size), the functionalities provided by the IMD may be minimized. The value of additional therapy or analysis is considered in light of the impact of the additional features on battery life. Consequently, in IMDs containing a non-rechargeable battery, battery life considerations may preclude providing additional therapy (e.g., more frequent electrical stimulation of tissue) or more computationally intensive analysis of a patient's condition that could ultimately benefit the patient. Rechargeable batteries allow for an increase in IMD energy use without a corresponding decrease IMD operational life, thereby enabling inclusion of features that may not be acceptable in an IMD powered by a non-rechargeable battery.

When using a rechargeable battery in an IMD, a battery recharging system is required. One system for recharging a battery in an IMD involves transcutaneous energy transmission. Transcutaneous energy transmission entails generation of a magnetic field external to the patient's body which induces current flow in a charging circuit of the implanted IMD. The IMD uses the induced current to charge the rechargeable battery.

Unfortunately, transcutaneous energy transmission is not without issues. The efficiency of transcutaneous energy transmission is affected by a number of physical variables. For example, charging efficiency is detrimentally affected if the IMD is not properly aligned with the external charger, or if the distance between the IMD and the external charger is too great. Furthermore, the magnetic field may induce current flow not only in the charging circuit of the IMD, but also in the metallic housing of the IMD. Current flow in the IMD housing is dissipated as heat. If the temperature of the housing becomes too high, the tissue surrounding the IMD may be damaged.

For these reasons, systems and methods for improving the efficiency of transcutaneous energy transmission to an IMD including a rechargeable battery are desirable.

BRIEF DESCRIPTION OF THE DRAWINGS

For a detailed description of exemplary embodiments of the invention, reference will now be made to the accompanying drawings in which:

FIG. 4a shows a diagram of oscillation for estimating system resonant frequency in accordance with various embodiments;

FIG. 5b shows a frequency spectrum corresponding to the sawtooth waveform of FIG. 5a;

NOTATION AND NOMENCLATURE

Figure 1:
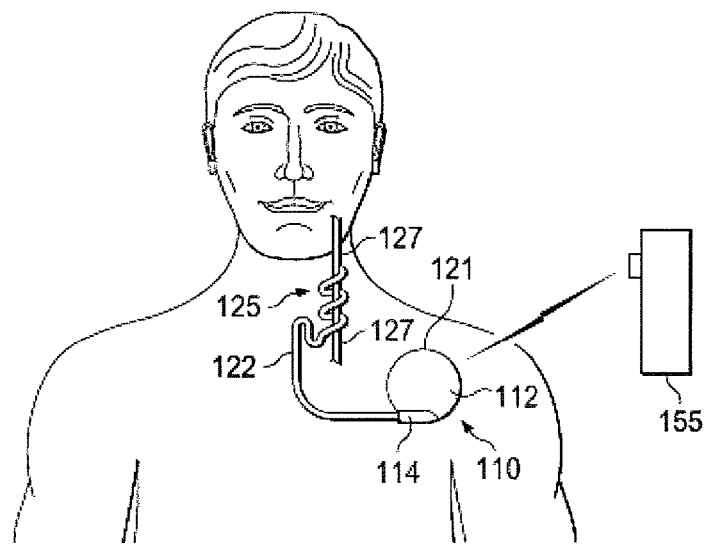
FIG. 1 shows an illustrative stimulation system coupled to a human cranial nerve in accordance with various embodiments of the invention.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections. Further, the term "software" includes any executable code capable of running on a processor, regardless of the media used to store the software. Thus, code stored in memory (e.g., non-volatile memory), and sometimes referred to as "embedded firmware," is included within the definition of software.

DETAILED DESCRIPTION

The following discussion is directed to various embodiments of the invention. The disclosed embodiments disclosed should not be interpreted, or otherwise construed, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Disclosed herein are various techniques for charging a rechargeable power cell, such as a rechargeable battery, in an implantable medical device ("IMD"). The impedance of a charging system used to transfer energy from a charging device to the IMD is minimized at the resonant frequency of the charging system. Consequently, optimum transfer of energy for charging a rechargeable power cell in the IMD is provided when the energy is transferred at the charging system resonant frequency. As the physical relationship between the IMD and the charging device changes, the resonant frequency of the charging system (which includes components of both the IMD and the recharging device) changes. The resonant frequency of the charging system is also subject to change based on variation in any one or more of a number of other variables, e.g., temperature and power cell loading. Each "side" of the recharging system will have its own resonant frequency: the primary side has one resonant frequency and the secondary side has a second resonant frequency. In each side, the resonant frequency is determined by the coil (i.e., an inductor), capacitors, resistors, and parasitic effects. When placed near each other in a recharging session, the primary and secondary sides also have a mutual inductance that substantially affects the system resonance. Optimum energy transfer generally occurs when the resonant frequencies for the primary and secondary sides are relatively close to each other. The resonant frequencies of each side do not need to match—but the system should be optimized to the typical use case (e.g., typical load, typical implant depth, typical placement and alignment, etc.). Some embodiments allow the system to self-tune the system's resonant frequency taking into account these numerous variables and interdependencies. Embodiments of the present disclosure employ various techniques for measuring the resonant frequency of the charging system and transferring energy from the charging device to the IMD at the measured resonant frequency. Thus, embodiments optimize energy transfer in the charging system, thereby improving charging efficiency, reducing charging time, and reducing undesirable dissipation of transferred energy as heat that may be detrimental to tissue surrounding the IMD.

Some embodiments of the present disclosure estimate the resonant frequency of the charging system by driving an electrical pulse (e.g., a single electrical pulse) into a primary coil of the recharging device and measuring the frequency of oscillation (i.e., ringing) induced by the pulse. The frequency of the oscillation approximates the resonant frequency of the charging system. The primary coil is then driven with a periodic signal at the estimated resonant frequency to transfer charging energy to the IMD. A wide variety of periodic signals may be used to drive the primary coil, e.g., sinusoidal, square, rectangular, triangular, sawtooth, stepped, etc. In further embodiments, an aperiodic or pseudo-periodic signal can be used to drive the primary coil.

Some other embodiments estimate the resonant frequency of the charging system by driving a periodic signal that sweeps across a range of frequencies. As the signal is driven into the primary coil and swept across the range of frequencies, the energy transferred from the recharging device to the IMD is measured. The sweep frequency at which energy transfer is maximized approximates the resonant frequency of the charging system. The primary coil is then driven with a periodic signal at the estimated resonant frequency to transfer charging energy to the IMD.

In yet other embodiments, the measured frequency of oscillation induced by a pulse, as described above, provides a rough approximation of the charging system resonant frequency. A narrow sweep signal (e.g., 100 hertz above and below) about the rough resonant frequency approximation provides a more precise estimate of the resonant frequency of the charging system. The primary coil is then driven with a periodic signal at the more precisely estimated resonant frequency to transfer charging energy to the IMD.

FIG. 1 illustrates an IMD 110 having a main body 112 comprising a metallic case 121 with a connector 114 for connecting to a lead assembly 122. The IMD 110 is implanted in a patient's chest in a pocket or cavity formed by the implanting surgeon just below the skin, similar to the implantation procedure for a pacemaker pulse generator. A stimulating nerve electrode assembly 125, preferably comprising an electrode pair, conductively couples to the distal end of an insulated and electrically conductive lead assembly 122, which preferably comprises a pair of lead wires (one wire for each electrode of an electrode pair). Lead assembly 122 is attached at its proximal end to the connector 114 on the case 121. The electrode assembly 125 is surgically coupled to a cranial nerve, such as a vagus nerve 127 in the patient's neck. The electrode assembly 125 preferably comprises a bipolar stimulating electrode pair, such as the electrode pair described in U.S. Pat. No. 4,573,481, which is incorporated herein by reference. Persons of skill in the art will appreciate that many electrode designs could be used in the present disclosure. The two electrodes are preferably wrapped around the vagus nerve, and the electrode assembly 125 preferably is secured to the nerve 127 by a spiral anchoring tether such as that disclosed in U.S. Pat. No. 4,979,511, which is incorporated herein by reference. Lead assembly 122 may be secured, while retaining the ability to flex with movement of the chest and neck, by a suture connection to nearby tissue.

The IMD 110 includes a power cell, such as a battery, for powering the IMD 110. The power cell may be charged after the IMD is implanted using an external charging device 155, which is external to the patient's body. The external charging device 155 may inductively couple with the IMD 110 to transfer charging energy to the IMD 110. The charging device 155 may be portable (e.g., handheld or configured to be secured to the patient's body in proximity to the IMD 110), or positionally fixed (e.g., at a location frequented by the patient). The external charging device 155 may also include a wireless communication system to facilitate radio frequency ("RF") or other communication between the external charging device 155 and the IMD 110. In some embodiments, the external charging device 155 communicates with the IMD 110 via one or more channels in the Medical Implant Communications Service ("MICS") bandwidths.

Figure 2:
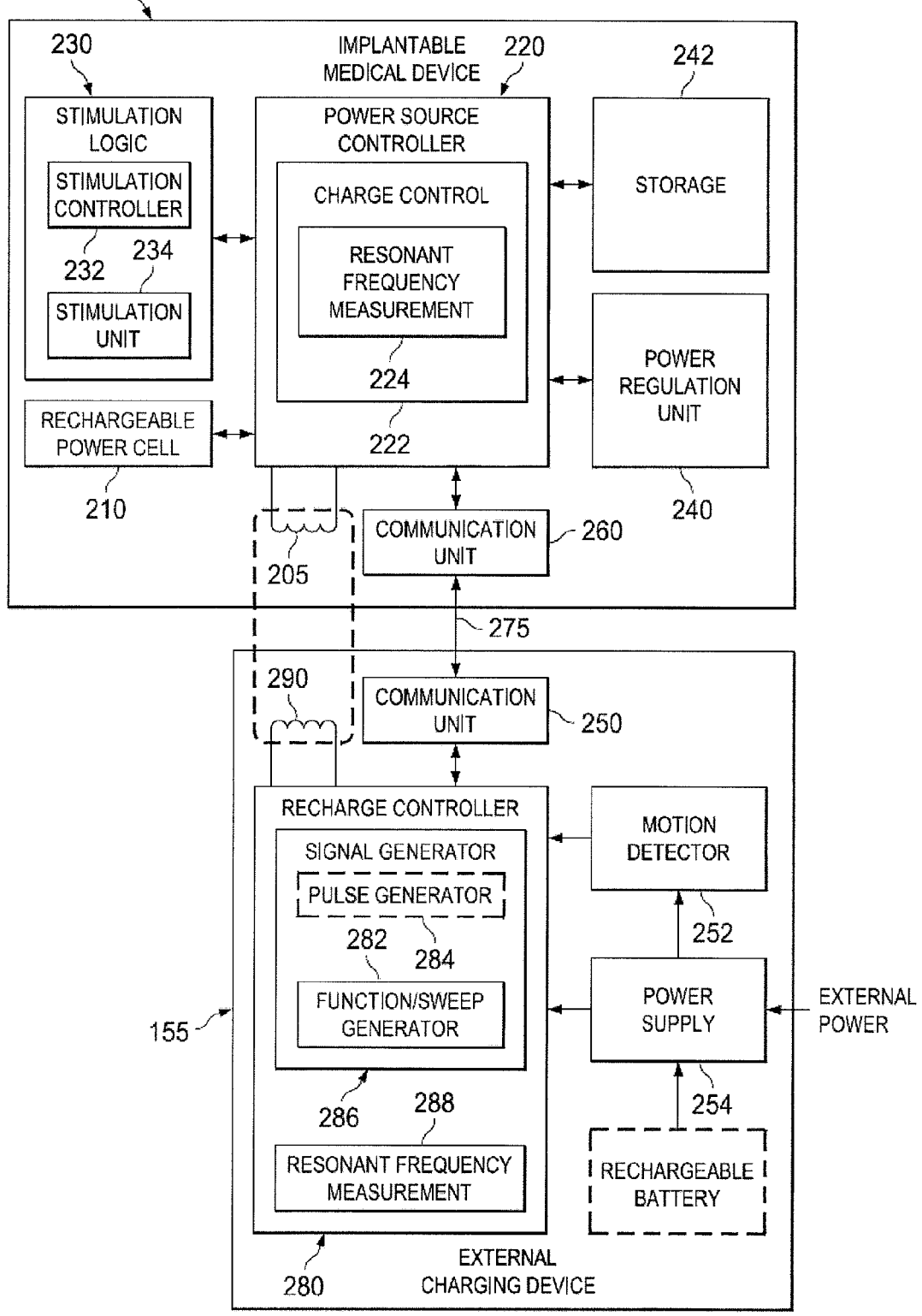
FIG. 2 shows a block diagram of the implantable medical device and the charging device shown in FIG. 1 in accordance with various embodiments of the invention.

FIG. 2 illustrates a block diagram of the IMD 110 and the external charging device 155 shown in FIG. 1 in accordance with various embodiments of the invention. In one embodiment, the IMD 110 comprises an inductor 205, a rechargeable power cell 210, a power-source controller 220 including a charge controller 222, a stimulation controller 232, a power regulation unit 240, a stimulation unit 234, a communication unit 260 and storage 242. The stimulation controller 232 and stimulation unit 234 together form stimulation logic 230. Storage 242 may be used for storing various program codes, starting data, and the like. The rechargeable power cell 210 may comprise a rechargeable battery. Other types of rechargeable power cells, such as capacitors, may also be used. The rechargeable power cell 210 provides power for the operation of the IMD 110, including electronic operations and stimulation bursts. The rechargeable power cell 210, in one embodiment, is a lithium-ion or other suitable rechargeable cell. The terminals of the rechargeable power cell 210 preferably electrically couple to the power-source controller 220 and the power regulation unit 240.

The inductor 205 is a coil of wire that generates an electrical current when exposed to magnetic flux. More specifically, the inductor 205 generates a current used to charge the rechargeable power cell 210 when the external charging device 155 generates a magnetic field detected by the inductor 205. The inductor 205 and associated components (e.g., a capacitor, not shown) preferably form a circuit tuned to match a resonant frequency of a corresponding inductor 290 in the external charging device 155. In some embodiments, the inductor 205 may be tuned to have a resonant frequency of approximately 10 kilohertz ("KHz").

The power-source controller 220 includes the charge controller 222 and additional circuitry for controlling and monitoring the flow of electrical power to various electronic and stimulation-delivery portions of the IMD 110 (such as the components 230, 240, 234, 260 and 242 illustrated in FIG. 2). The charge controller 222 includes various components for providing charging current to the rechargeable power cell 210. The charge controller 222 may include rectifiers, filter capacitors, and the like for generating a direct current from the alternating current provided by the inductor 205. The charge controller 222 also controls the levels of voltage and current provided to the power cell 210 during charging to ensure proper charging and to prevent overcharging. The power-source controller 220 is capable of monitoring the power consumption or charge depletion of the IMD 110, measuring the voltage across the replaceable power cell 210, and generating recharge notifications and/or elective replacement and/or end-of-service signals.

In some embodiments, the charge controller 222 includes a resonant frequency measurement unit 224. The resonant frequency measurement unit 224 is configured to monitor one or more parameters of the energy transferred from the external charging device 155, and to determine therefrom an indication of the resonant frequency of the charging system comprising the IMD 110 and the external charging device 155. The resonant frequency measurement unit 224 may measure the frequency of oscillation induced by the external charging device, and/or measure power provided by the inductor 205 during a sweep signal induced by the external charging device 115 to provide an estimate of the charging system resonant frequency. Consequently, the resonant frequency measurement unit 224 may include power measurement circuitry and/or frequency measurement circuitry. Power measurement circuitry includes current and/or voltage sensors and the like as known in the art. Frequency measurement circuitry includes timers to time the period of the oscillation, processing circuitry to perform Fourier analysis, and/or other frequency measurement systems known in the art. A resonant frequency estimate or an indication of the resonant frequency of the charging system generated by the resonant frequency measurement unit 224 may be communicated to the external charging device 155 via the communication unit 260.

The impedance measured at the input to the inductor 290 is a function of the impedances of the inductor 290, mutual inductance, inductor 205, and load presented to the inductor 205 by the circuitry of the IMD 110 (i.e., secondary load). The impedances of the inductors 290, 205 do not vary significantly but the mutual inductance varies as a function of distance between and alignment of the inductors 290, 205, and other environmental factors.

For a given mutual inductance and given secondary load, the current drawn by the inductor 290 has a known variation with frequency around the system's resonance point, where the system includes the IMD 110 and the external charging device 155. If operational conditions are constant and known, such that the mutual inductance is known, then a set of measurements of the primary current drawn by the inductor 290 as a function of frequency can be matched to measurements obtained under the same conditions with the same mutual inductance for a given secondary load. Therefore, through correlation, the secondary load can be determined and if the voltage on the IMD 110 is held constant, for example, by power regulation unit 240, the power delivered to the inductor 205 can be determined.

A frequency of oscillation induced in the inductor 205 can be measured. The signal may be attenuated due to losses in the system and it may be filtered somewhat, but the resonant frequency component is measurable. To measure a frequency of an induced oscillation in the inductor 205, the voltage waveform produced by the inductor 205 may be sampled at, for example, at least 10× the resonant frequency, (e.g., approximately 100 KHz in some embodiments), a Fourier transform of the sampled waveform is computed, and the highest amplitude frequency component of the transformed waveform should represent the resonant frequency. This resonant frequency value may then be transmitted from the IMD 110 to the external charging unit 155 via communication 275 and the charging frequency will be adjusted to match this resonant frequency.

The communication unit 260 facilitates communication between the IMD 110 and the external charging device 155, as shown. The communication unit 260 may comprise hardware (e.g., RF circuitry), software, firmware or any combination thereof. Communications between the external charging device 155 and the communication unit 260 may occur via a wireless or other type of communication, illustrated generally by line 275 in FIG. 2.

The power regulation unit 240 is capable of regulating power (e.g., limiting current and/or voltage) delivered by the rechargeable power cell 210 to particular components of the IMD 110 according to their needs and functions. The power regulation unit 240 may perform a voltage conversion to provide appropriate voltages and/or currents for the operation of the components. The power regulation unit 240 may also be configured to regulate charging voltage and/or current provided to the rechargeable power cell 210 during charging. The power regulation unit 240 may comprise hardware, software, firmware or any combination thereof.

Stimulation controller 232 defines the electrical stimulation pulses to be delivered as part of a burst to the nerve tissue 127 according to parameters and waveforms that may be programmed into the controller 232 prior to or after implantation of the IMD 110 into the patient's body. The stimulation controller 232 controls the operation of the stimulation unit 234, which generates the stimulation pulses comprising a burst according to the parameters defined by the stimulation controller 232 and, in some embodiments, provides these pulses to the lead assembly 122 and electrode assembly 125. Stimulation pulses provided by the IMD 110 may vary widely across a range of parameters. The stimulation logic 230, the stimulation controller 232, and the stimulation unit 234 may comprise discrete hardware circuitry, or software executed by a processor, or any combination thereof.

Referring still to FIG. 2, the external charging device 155 includes an inductor 290, communication unit 250, a motion detector 252, a power supply 254, and a recharge controller 280. The recharge controller 280 further includes a signal generator 286 and a resonant frequency measurement unit 288. The inductor 290 is a coil of wire that generates a magnetic field when electrical current flows through the inductor 290. More specifically, the inductor 290 generates magnetic flux that induces the flow of charging current in the inductor 205 of the IMD 110 in response to drive current from the recharge controller 280.

Figure 3:
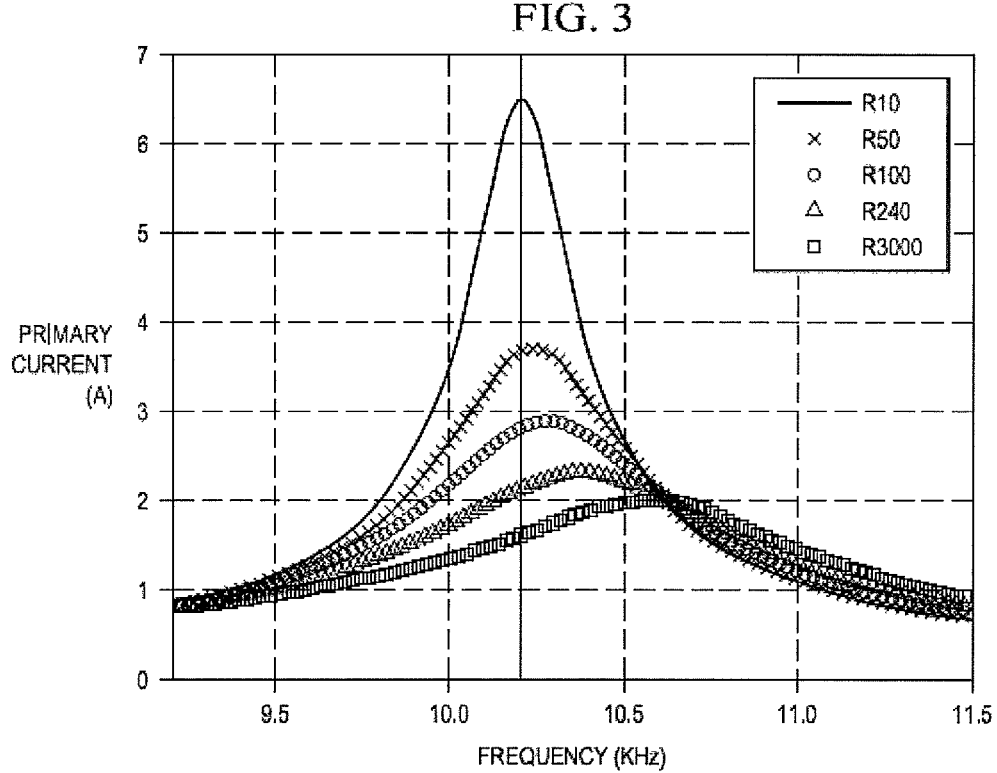
FIG. 3 shows an example of how optimal charging frequency and charging system bandwidth change based on changes in a charging system variable.

Inductive coupling between the inductors 290 and 205 is a near-field effect that operates only over short distances. At the distances over which the inductors 290, 205 inductively couple, there is significant electromagnetic interaction between the inductors 290, 205 and other conductive or ferrous components (e.g., the metallic case 121 of the IMD 110). Changes in the relative location of the inductors 290, 205, or other interacting conductive or ferrous components, or changes in other variables (e.g., the equivalent load of the power cell 210) cause the resonant frequency and bandwidth of the charging system to change. In a charging system that drives the primary coil (e.g., the inductor 290) at a constant frequency, the narrowing bandwidth and changing resonant frequency may result in a significant reduction in energy transferred to the secondary coil (e.g., the inductor 205). FIG. 3 graphically illustrates how the optimal charging frequency and charging system bandwidth change based on changes in one system variable—in this case, changes in the power cell 210 equivalent load. The vertical axis of FIG. 3 shows the amount of current delivered to the primary coil (e.g., inductor 290) and the horizontal axis represents the frequency. Here, all variables on the primary side of the system were kept constant. On the secondary side, the voltage and current is left floating (these values will settle based on the energy transferred from the primary) and the power cell load inside the IMD 110 (e.g., power cell 210) is varied from 10 to 3,000 Ohms. This changing impedance inside the IMD 110 results in different levels of current delivered to the primary coil housed in the external charging device 155. Because inductively coupled recharging is often a lossy relationship, in practice, only a portion of the current delivered to the external primary coil will be induced in the implanted secondary coil. FIG. 3 illustrates how changing the load in the IMD changes the bandwidth and resonant frequency of the entire system. Similar changes are seen when changing other system variables, as discussed above. For example, the power delivered, bandwidth, and resonant frequency can all change as the distance from the primary coil to the secondary coil changes or the two coils change in alignment. Because the system has a fairly narrow bandwidth and the resonant frequency of the system changes with changes in the parameters, the ability to adjust the drive frequency allows for improved system performance across a wide range of conditions. In order to optimize charging of the power cell 210, the frequency of energy transferred from the external charging device 155 to the IMD 110 should be based on (e.g., equal to) the changing resonant frequency of the charging system.

FIG. 3 illustrates various implementation considerations related to embodiments of the charging system disclosed herein. In one embodiment, the system is designed to have very high efficiency and a high Q. The amount of current driven into inductor 290, as depicted in FIG. 3, is a useful measure to estimate the efficiency of the system. Here, the curve R10 represents a high Q system, which, at resonance, is capable of transmitting more energy than curve R3000. Since Q and bandwidth are linked, changes in system variables can result in changes in bandwidth as well. For example, curve R10 represents a narrower bandwidth than the bandwidth for curve R3000. As explained further herein, the system bandwidth is related to the ability of inducing oscillation in inductor 290.

Returning now to FIG. 2, the signal generator 286 of the recharge controller 280 includes a pulse generator 284 and a function/sweep signal generator 282. The signal generator 286 provides drive signals (i.e., drive current) to the inductor 290. The magnitude and frequency of the magnetic field generated by the inductor 290 are controlled, at least in part, by the magnitude, frequency, and duty cycle of the drive signals generated by the signal generator 286. To optimize energy transfer between the external charging device 155 and the IMD 110, the signal generator 286 can vary the frequency of the drive signals provided to the inductor 290 in accordance with an estimated resonant frequency of the charging system including portions of the IMD 110 and the external charging device 155. Accordingly, the function/sweep signal generator 282 may include a voltage controlled oscillator ("VCO"), a digital function generator, or the like to generate frequency variant waveforms for driving the inductor 290. The recharge controller 280 may provide a frequency value to the digital function generator or a voltage to the VCO of the function/sweep generator 282 that causes the function/sweep generator 282 to generate a drive signal according to the estimated resonant frequency. A wide variety of waveforms can be created by the function/sweep generator 282 including, for example, sinusoidal, square, rectangular, triangle, sawtooth, stepped, and other waveforms. These waveforms can be periodic, aperiodic, or pseudo-periodic waveforms and can be produced at a wide variety of fixed, variable, transient, random, or sweeping frequencies. One skilled in the art will understand that the function/sweep generator 282 can generate electrically equivalent drive signals using either voltage waveforms or current waveforms.

The recharge controller 280 may estimate the system resonant frequency using one or more estimation techniques. The pulse generator 284 can drive a one or more pulses or steps into the inductor 290 at the direction of the recharge controller 280. The pulse induces oscillation in the in the inductor 290 at a frequency that is at or near the resonant frequency of the charging system. FIG. 4a shows an illustration of oscillation 400 (e.g., a damped oscillation as shown, or a steady state oscillation) produced by driving a pulse into the inductor 290. Oscillation 400 will frequently be a damped oscillation, but it will not always be damped. For example, oscillation 400 would not appear damped if: a new pulse was supplied near the end of oscillation 400's first period, the system was a passive lossless system, or the system was an active system with a positive feedback loop. By design and/or manufacture, the inductors 290, 205 are preferably tuned to relatively close resonant frequencies, which take into account the mutual inductance between inductors 290 and 205. In a poorly designed system, it is possible for the resonance of the inductor 290 to dominate and cause the frequency of the oscillation to be closer to the self-resonant frequency of the inductor 290 than to the resonant frequency of the charging system. The resonant frequency of the primary coil's side is preferably tuned anticipating the most typical use case (and accounting for the mutual inductance and parasitic effects), and often tends to be relatively close to the resonant frequency of the secondary coil's side. The resonant frequency for the primary side depends on more than just inductor 290 because other components (e.g., capacitors and resistors) and parasitic effects may significantly change the resonant frequency. Accordingly, references herein to tuning the resonant frequency of inductor 290 generally refer to tuning the resonant frequency for the entire primary side. Similarly, references herein to tuning the resonant frequency of inductor 205 generally refer to tuning the resonant frequency for the entire secondary side. Likewise, one skilled in the art will recognize that discussions of bandwidth, energy transfer, and efficiency inherently include these additional components and parasitic effects even if the discussion appears to be limited to inductors 290 and 205 (or the primary and secondary coils).

Figure 4B:
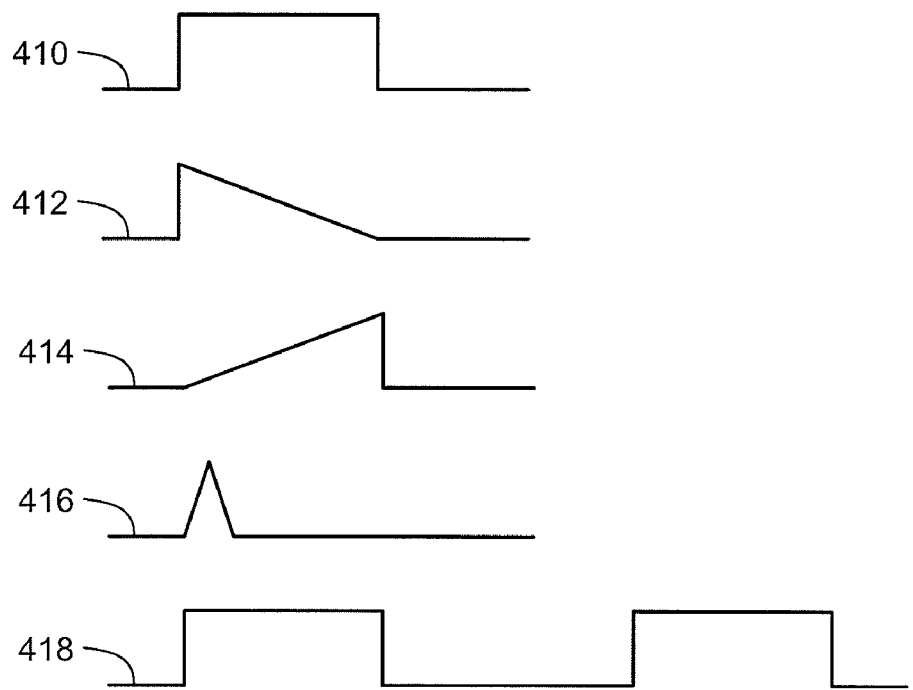
FIG. 4b shows an illustration of exemplary pulses capable of inducing oscillation in an inductor.

The pulse supplied to inductor 290 by pulse generator 284 can be a variety of waveform shapes. FIG. 4b shows an illustration of exemplary pulses capable of inducing oscillation in the inductor 290. Pulses 410, 412, 414, 416, and 418 can be a voltage waveform or a current waveform. Pulse 410 illustrates either a square pulse or rectangular pulse depending on the duty cycle. Pulse 412 is sawtooth pulse and pulse 414 is another sawtooth pulse, but in the reverse direction. Pulse 416 is a triangular pulse. Pulse 418 is a rectangular pulse that is a periodic waveform. Other examples include sinusoidal, stepped, and other waveforms. The waveforms can be a single pulse (e.g., a periodic waveform that only lasts for up to one period), periodic waveforms (e.g., pulse 418), aperiodic waveforms, or pseudo-periodic waveforms. Various embodiments use these exemplary pulses or similar pulses.

Figure 4C:
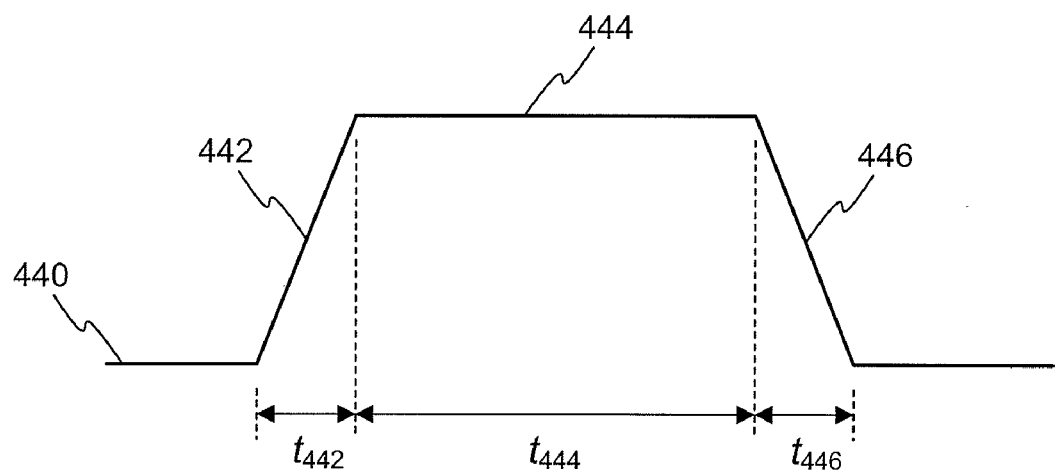
FIG. 4c shows an exemplary square pulse for inducing oscillation in an inductor.

In one embodiment, pulse generator 284 creates a pulse having a rising or falling edge steep enough such that the frequency spectrum contains components in the low frequency range up to at least greater than or equal to the resonant frequency to which inductors 290 and 205 are tuned, inclusive of frequencies in between. FIG. 4c shows a square pulse 440 having a rising edge 442 with its corresponding rise time duration of $t_{442}$, flat portion 444 with its corresponding time duration of $t_{444}$, and falling edge 446 with its corresponding fall time duration of $t_{446}$. The square waveform's bandwidth, which is approximately the frequency of the square waveform's highest frequency component with significant energy, is approximately 1/(3*Rise Time). Accordingly, in the case of a square wave, the relationship between the desired rise time of the pulse and the system's resonant frequency is approximately: $f_0=1/(3*\text{Rise Time})$. Or, stated differently: Rise Time=$1/(3*f_0)$. The term "Rise Time" can be replaced with "Fall Time" in these equations for the square waveform. Therefore, if the resonant frequency of the system is designed to be about 10 KHz, then oscillation may be induced in inductor 290 when $t_{442}$ and/or $t_{446}$ are about 33 microseconds (μs). That is, an optimum rise time or fall time for a system with a 10 KHz resonant frequency is approximately 33 μs or possibly less when using a square waveform. Similarly, if the resonant frequency of the system is designed to be about 2.4 GHz, then oscillation may be induced in inductor 290 when $t_{442}$ and/or $t_{446}$ are about 138.89 picoseconds (μs) when using a square waveform. Accordingly, the resonant frequency of the system is related to the amount of time it takes the rising edge to rise or falling edge to fall if oscillation is to be induced in inductor 290. In another embodiment, the rise time and/or fall time are much shorter than the computed minimum for a given resonant frequency (e.g., 10 μs, 1 μs, 0.1 μs, or faster when the resonant frequency is 10 KHz). In yet another embodiment, the rise time and/or fall time are only marginally shorter than the computed minimum for a given resonant frequency (e.g., 10% faster). Other embodiments may use pulses other than square waveforms to induce oscillation, and different pulses may have a different relationship between the system's resonant frequency and the rise time/fall time of the pulse. The principle remains the same, however, that the duration, or "steepness," of the pulse's rise time and/or fall time affects the ability to induce an oscillation at a given system resonant frequency.

Figure 5A:
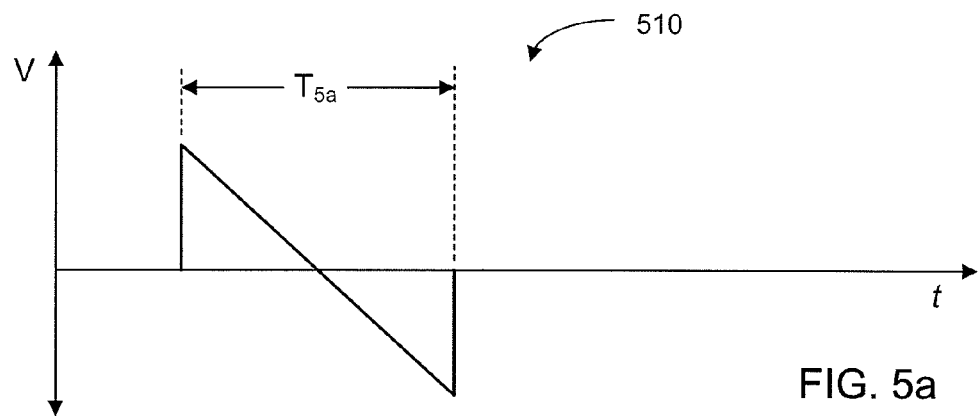
FIG. 5a shows an exemplary sawtooth waveform for inducing oscillation in an inductor.
Figure 5B:
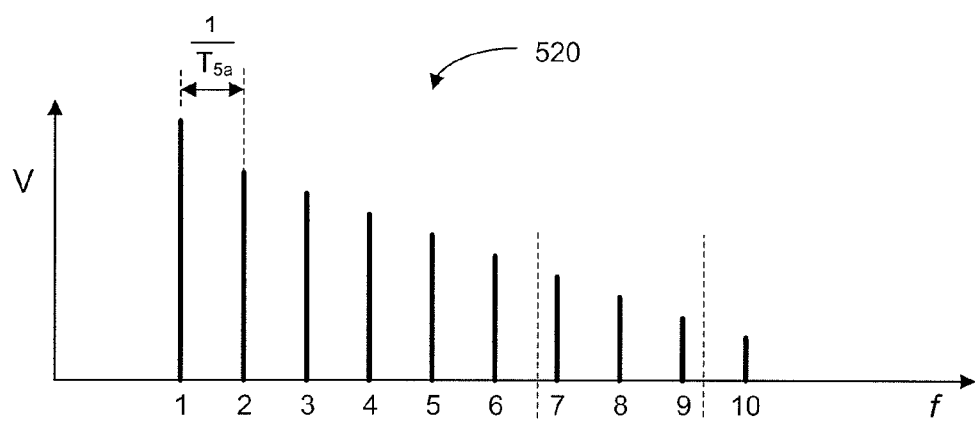
Figure 5C:
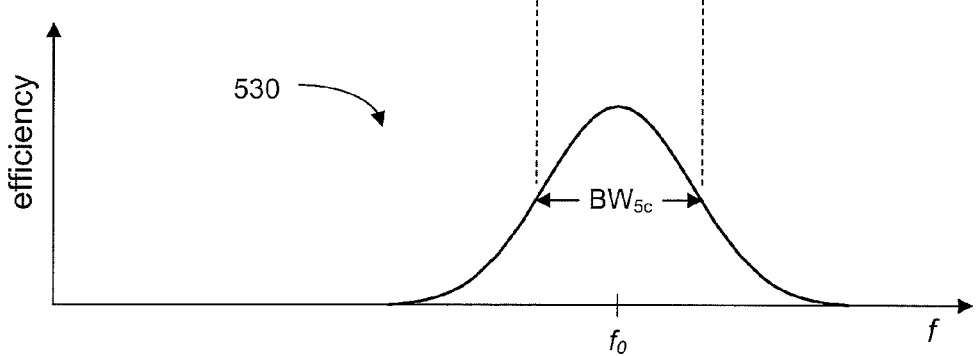
FIG. 5c shows exemplary energy transfer relative to the frequencies of the sawtooth waveform.

In one embodiment, the shape of the pulse is based on the system bandwidth. FIG. 5a illustrates a sawtooth waveform with a period $T_{5a}$ supplied to inductor 290. The sawtooth waveform 510 in FIG. 5a is actually the sum of numerous different sinusoidal waveforms of different frequencies (i.e., a harmonic frequency) and amplitudes. These separate waveforms can be viewed on a frequency spectrum plot 520, as shown in FIG. 5b, which represents the numerous frequencies with attenuating amplitudes. For sawtooth waveform 510 the harmonics are spaced apart by $1/T_{5a}$ and are spaced one harmonic apart (i.e., both odd and even harmonics). In order to induce oscillation in inductor 290, the harmonics should be spaced close enough together that at least one harmonic falls within the system's bandwidth. FIG. 5c plots the energy transfer 530 across frequencies, which shows the system bandwidth $BW_{5c}$ centered around the resonant frequency. Comparing FIGS. 5b and 5c shows that sawtooth waveform 510 should induce oscillation because more than one harmonic falls within the system bandwidth $BW_{5c}$ (three harmonics in this case).

In another embodiment, the shape of the pulse is designed to anticipate a system bandwidth that narrows or widens. As described in FIG. 3 and its related discussion, many variables can affect the system bandwidth and overall efficiency. A high Q system has a narrower bandwidth than a system with a lower Q. The pulse designed to induce oscillation in inductor 290 may be designed to have harmonics spaced close enough so that as the system bandwidth changes, at least one harmonic should still fall within the narrowest expected system bandwidth.

Figure 5D:
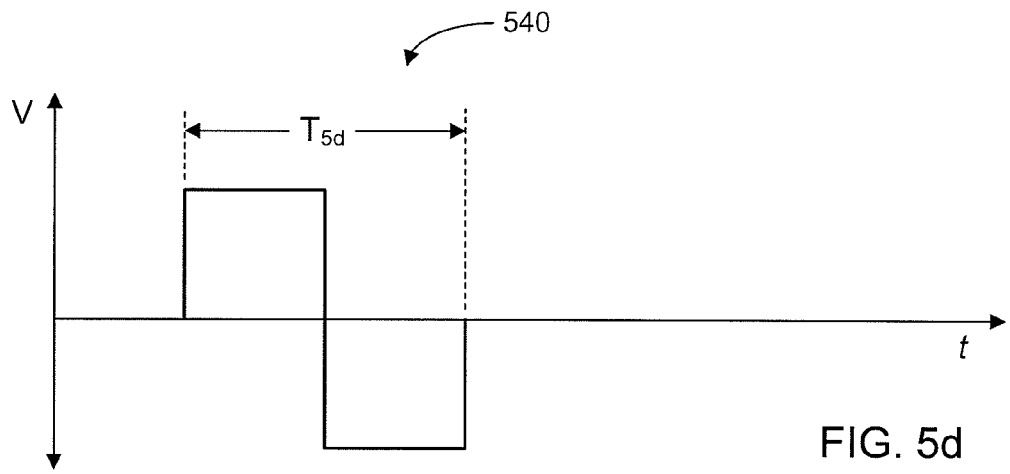
FIG. 5d shows an exemplary square waveform for inducing oscillation in an inductor.
Figure 5E:
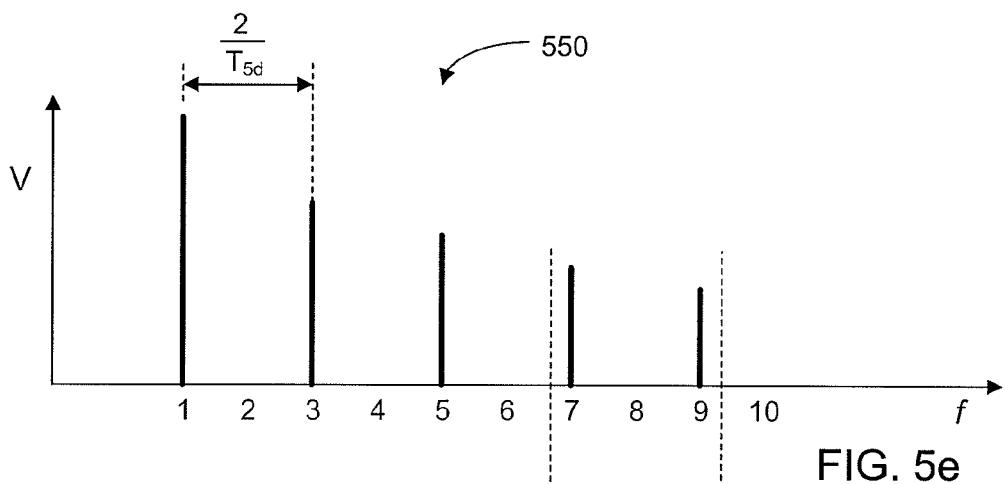
FIG. 5e shows a frequency spectrum corresponding to the square waveform of FIG. 5d.
Figure 5F:
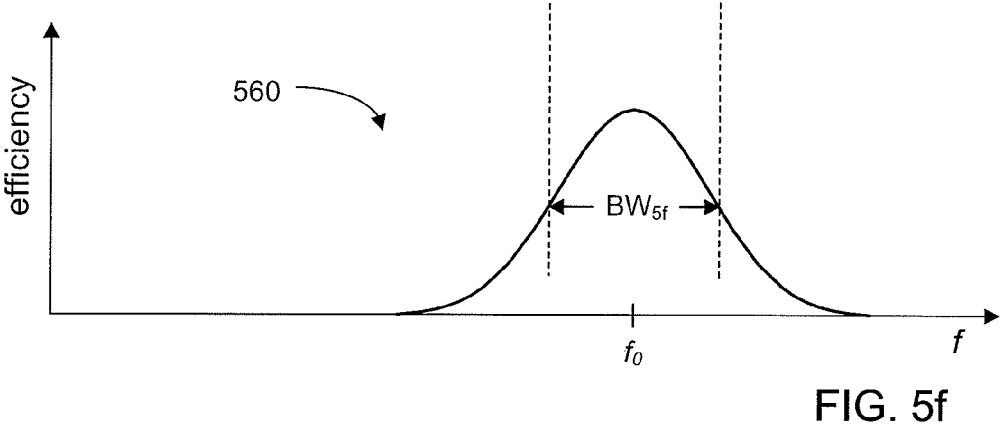
FIG. 5f shows exemplary energy transfer relative to the frequencies of the square waveform.

In another embodiment, the oscillation is designed to be induced by a square waveform. FIG. 5d illustrates a square waveform with a period $T_{5d}$ supplied to inductor 290. The square waveform 540 in FIG. 5d is actually the sum of numerous different sinusoidal waveforms of different frequencies (i.e., harmonic frequencies) and amplitudes. These separate waveforms can be viewed on a frequency spectrum plot 550, as shown in FIG. 5e, which represents the numerous frequencies with varying amplitudes. For square waveform 540, the harmonics are spaced apart by $2/T_{5d}$, which is every other harmonic (typically the odd harmonics depending on the shape of the square waveform). In order to induce oscillation in inductor 290, the harmonics should be spaced close enough together that at least one harmonic falls within the system's bandwidth around the resonant frequency and for a variety of other possible resonant frequencies. FIG. 5f plots the energy transfer 560 across frequencies, which shows the system bandwidth $BW_{5f}$ centered around the system's resonant frequency. Comparing FIGS. 5e and 5f shows that square waveform 540 should induce oscillation because more than one harmonic (with sufficient energy) falls within the system bandwidth $BW_{5f}$ (two harmonics in this case).

In one embodiment, the shape of the pulse is determined by the range of possible resonant frequencies. For example, the pulse would be a waveform that had at least all of the frequency components that covered the range of possible resonant frequencies. The pulse would be a sum of all those frequency components and the resulting Fourier series summation would represent the waveform used as the pulse. This approach could cut out all the low frequency components which are so far below the resonant frequency that they will never contribute towards inducing oscillation. Depending on the range of possible resonant frequencies, the shape of this pulse could change appreciably from one system to the next, over time in the same system, or during a single recharging session as, for example, the patient moves around. In another embodiment the pulse would be a waveform that had only the frequency components that covered the range of possible resonant frequencies.

In another embodiment pulse generator 284 is omitted from signal generator 286 because function/sweep generator 282 outputs a drive signal sufficient to induce oscillation in inductor 290. For example, function/sweep generator outputs a square waveform similar to the one shown in FIG. 4c where the rising edge and/or the falling edge are sufficiently fast to induce oscillation in inductor 290. In such an embodiment pulse generator 284 is not needed and its function can be performed by function/sweep generator 282.

The resonant frequency measurement unit 288 includes logic and circuitry that measures the frequency of the oscillation. Some embodiments of the resonant frequency measurement unit 288 detect the peaks of each cycle of the oscillation, measure the peak-to-peak time intervals (i.e., the wave period), and estimate the system resonant frequency based on the measured peak-to-peak time intervals. In some embodiments, the frequency of the oscillation is measured using various full-wave, half-wave, or quarter-wave measurement methods. For example, frequency measurement unit 288 can operate by measuring the time interval between any peak, valley, zero crossing, or the like of the oscillation (e.g., valley to valley, peak to valley, valley to peak, valley to zero crossing, peak to zero crossing, zero crossing to zero crossing, etc.). Still other embodiments measure the period of the oscillation by converting the oscillation to a square wave and timing the period of the square wave. Yet other embodiments apply Fourier analysis to the waveform and determine therefrom a fundamental frequency of the oscillation.

The resonant frequency measurement unit 288 may also determine the resonant frequency of the charging system based on a drive signal that sweeps across a range of frequencies including the resonant frequency. Specifically, the recharge controller 280 may direct the function/sweep generator 282 to create a drive signal sweeping across a range of frequencies encompassing the system resonant frequency and to provide the drive signal to the inductor 290. For example, if the system is designed to have a resonant frequency of 10 KHz, then the recharge controller 280 can direct the function/sweep generator 282 to generate a sweeping drive signal having a range of 8-13 KHz and to provide the drive signal to the inductor 290 at a specified rate of frequency change. In one embodiment, the resonant frequency measurement unit 224 monitors the energy transferred to the inductor 205 during the sweep and identifies the frequency corresponding to maximum energy transfer (e.g., by identifying the time at which energy transfer is maximized which is correlated with frequency based on sweep range, rate, and start time). In another embodiment, the resonant frequency measurement unit 288 monitors the energy transferred from the inductor 290 during the sweep and identifies the frequency corresponding to maximum energy transfer (e.g., by identifying the time at which energy transfer is maximized which is correlated with frequency based on sweep range, rate, and start time). In further embodiments, the range of frequencies covered during the sweep are very narrow (e.g., 9.95 KHz to 10.05 KHz), relatively narrow (e.g., 8 KHz to 13 KHz), wide (e.g., 5 KHz to 1 GHz), or very wide (e.g., 3 KHz to 5 GHz). In still further embodiments, only a subset of the frequencies within the sweep range are selected to be driven, where the selection is based on an algorithm, system input, user input, or predetermined method. Some embodiments of the resonant frequency measurement unit 224 or 288 determine the sweep signal frequency of maximum energy transfer by measuring the current flowing through the inductor 205 or 290 and comparing the measurement values. Embodiments may apply any method of measuring inductor power output and determining a maximum value known in the art.

As shown in FIG. 2 and explained above, at least one of the IMD 110 and the external charging device 155 includes an embodiment of a resonant frequency measurement unit. 224, 288. Some embodiments of the IMD 110 and the external charging device 155 omit the resonant frequency measurement unit. Various embodiments of the resonant frequency measurement unit 224, 288 may include different measurement circuitry and capabilities. For example, the resonant frequency measurement unit 288 may include only circuitry for measuring the frequency of oscillation, while the resonant frequency measurement unit 224 may include only circuitry for measuring power transfer from the charging device 155.

In some embodiments, the energy transferred to the IMD 110 during the sweep signal is measured in the resonant frequency measurement circuit 224 of the IMD 110. The IMD 110 can provide information indicative of the frequency of maximum energy transfer during the sweep signal to the external charging device 155. The information may include any information indicative of the system resonant frequency, including received power measurements, time of maximum energy transfer, frequency of maximum energy transfer, etc. The recharge controller 280 programs the function/sweep generator 282 to drive the inductor 290 based on the estimated system resonant frequency derived from the information received from the IMD 110.

In another embodiment, the recharge controller 280 uses both the pulse generator 284 and the function/sweep generator 282 to accelerate estimation of the charging system resonant frequency. A resonant frequency estimation based solely on the frequency of oscillation induced by pulsing the inductor 290 can be performed relatively quickly but may be less accurate than estimation based on a sweep signal driven into the inductor 290. However, driving a sweep over a range of frequencies adequate to encompass all possible variations in system resonant frequency (e.g., hundreds or thousands of KHz) at a rate allowing accurate measurement of energy transfer may consume too much time or power. Therefore, some embodiments of the recharge controller 280 reduce the time needed to accurately estimate the system resonant frequency, by first causing the pulse generator 284 to drive a pulse into the inductor 290 and causing the resonant frequency measurement unit 288 to determine the frequency of the oscillation produced by the pulse as explained above. The recharge controller 280 thereafter programs the function/sweep generator 282 to generate a drive signal that sweeps over a narrow range of frequencies based on (e.g., centered at) the determined frequency of the oscillation. The recharge controller 280, via resonant frequency measurement unit 224, determines the frequency of maximum energy transfer (i.e., the system resonant frequency) based on the sweep signal as described above. Because the frequency of the oscillation provides a good starting estimate for the system resonant frequency, the sweep signal may encompass a smaller frequency range than would be needed otherwise. For example, in some embodiments a sweep signal having a range of 100 hertz or less about the frequency of oscillation may be sufficient to accurately identify the charging system resonant frequency. Sweep time corresponds to sweep range, and consequently reducing the sweep range reduces the time required to accurately determine charging system resonant frequency.

The recharge controller 280 may measure and change the frequency of the drive signal provided to the inductor 290 any number of times during a charging session. The recharge controller 280 may initiate resonant frequency measurement on a periodic basis (e.g., once per second), or based on information indicating that the resonant frequency of the charging system may have changed. For example, if energy transfer measurement circuitry in either the external charging device 155 or the IMD 110 identifies an unplanned change (e.g., an unplanned reduction) in energy transfer, possibly indicating a change in the charging system, then the recharge controller 280 may initiate resonant frequency measurement and change the frequency of the signal driving the inductor 290 accordingly. Additionally, some embodiments of the external charging device 155 include the motion sensor 252. Relative motion of the external charging device 155 and the IMD 110 may be indicative of a change in charging system resonant frequency. If the motion sensor 252 detects movement of the external charging device 155 or movement of the external charging device 155 relative to the IMD 110, then the recharge controller 280 may initiate resonant frequency measurement and drive signal frequency correction. The motion sensor 252 may include an accelerometer, a gyroscope, an optical detector, a sonic detector, or other type of detector employed with motion detection techniques known in the art. For example, if the motion sensor 252 is a 3-axis accelerometer, then the recharge controller 280 may be configured to monitor the output of the accelerometer during a charging session. Any change in acceleration, or any change in acceleration above a predetermined threshold, detected by the recharge controller 280 may be deemed to indicate possible repositioning of the external charging device 155. The recharge controller 280 may initiate resonant frequency measurement based on the detected change in acceleration.

The recharge controller 280 and each of the resonant frequency measurement unit 288, pulse generator 284, and function/sweep generator 282 may include hardware (e.g., processors, integrated circuits, etc.), software programming, or a combination thereof.

The communication unit 250 facilitates communication between the external charging device 155 and the IMD 110. Information transferred between the external charging device 155 and the IMD 110 may include system resonant frequency measurement information (e.g., measurement initiation information, measurement result information, etc.) and power cell 210 charge state information. The communication unit 250 may include RF circuitry, filters, amplifiers, transceivers, and the like that comprise hardware, software, firmware or any combination thereof. Communications between the communication units 250, 260 may be via wireless or other type of communication.

The power supply 254 provides power for the operation of the external charging device 155 and for recharging the IMD 110. The power supply 254 may be connected to the alternating current ("AC") power mains or to a direct current ("DC") power supply external to the device 155 (e.g., a universal serial bus port of a computer). The power supply 254 may include AC-DC converters, DC-DC converters, voltage/current regulators, filters, etc. The power supply 254 may also include a rechargeable battery, which may allow the patient to first charge the external charging device 155 and then charge the IMD 110 without being tethered to a power cord connected to an outlet.

Figure 6:
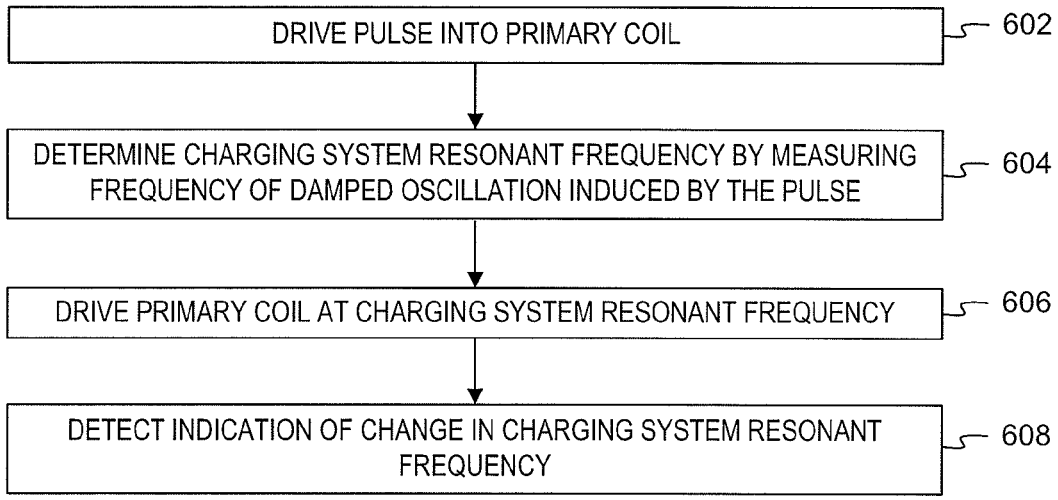
FIGS. 6-13 show flow diagrams of illustrative methods for charging a rechargeable power cell in the implantable medical device as shown in FIG. 1 in accordance with various embodiments.

FIG. 6 shows a flow diagram of an illustrative method for charging the rechargeable power cell 210 in the IMD 110 based on a charging system resonant frequency estimate made in an external charging device 155 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 6, as well as other operations described herein, can be implemented as instructions stored in a computer readable medium and executed by a processor.

In block 602, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 causes the signal generator 226 to drive a pulse or a step signal into the inductor 290. The pulse induces oscillation in the inductor 290.

In block 604, the resonant frequency measurement unit 288 determines the frequency of the oscillation. The frequency of the oscillation is at or near the resonant frequency of the charging system. Any suitable frequency measurement technique, such as Fourier analysis or cycle time measurement may be used to determine the fundamental frequency of the oscillation.

In block 606, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 608, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 7:
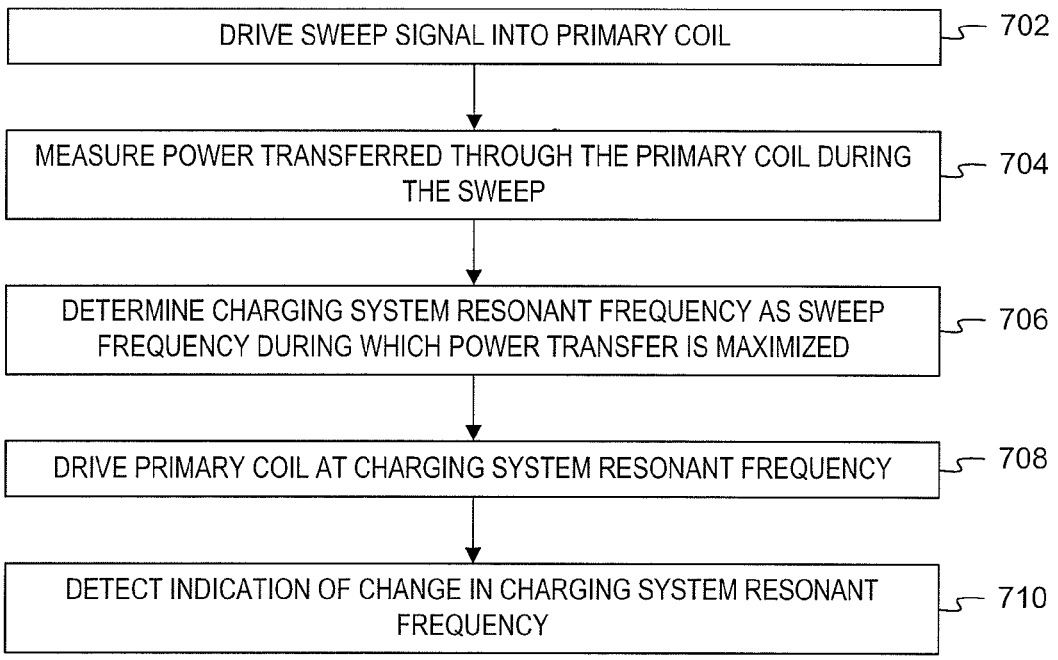

FIG. 7 shows a flow diagram of an illustrative method for charging the rechargeable power cell 210 in the IMD 110 based on a charging system resonant frequency estimate made in an external charging device 155 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 7, as well as other operations described herein, can be implemented as instructions stored in a computer readable medium and executed by a processor.

In block 702, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 programs (or otherwise directs) the function/sweep generator 282 to drive a sweep signal into the inductor 290.

The start frequency and frequency range of the sweep signal can vary, but are intended to encompass the resonant frequency of the charging system. In some embodiments, the sweep signal may be programmed to encompass the expected variation in charging system resonant frequency (e.g., 8-13 KHz). In some embodiments, the sweep frequency range is centered on a frequency to which the inductor 290 is tuned.

In block 704, as the sweep signal is driven into the inductor 290, the resonant frequency measurement unit 288 measures the power transferred through the inductor 290.

In block 706, the resonant frequency measurement unit 288 determines the resonant frequency of the charging system based on measurements of power transferred through the inductor 290 during the sweep. The frequency of the sweep at which power transfer is maximized may be deemed the charging system resonant frequency.

In block 708, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 710, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 8:
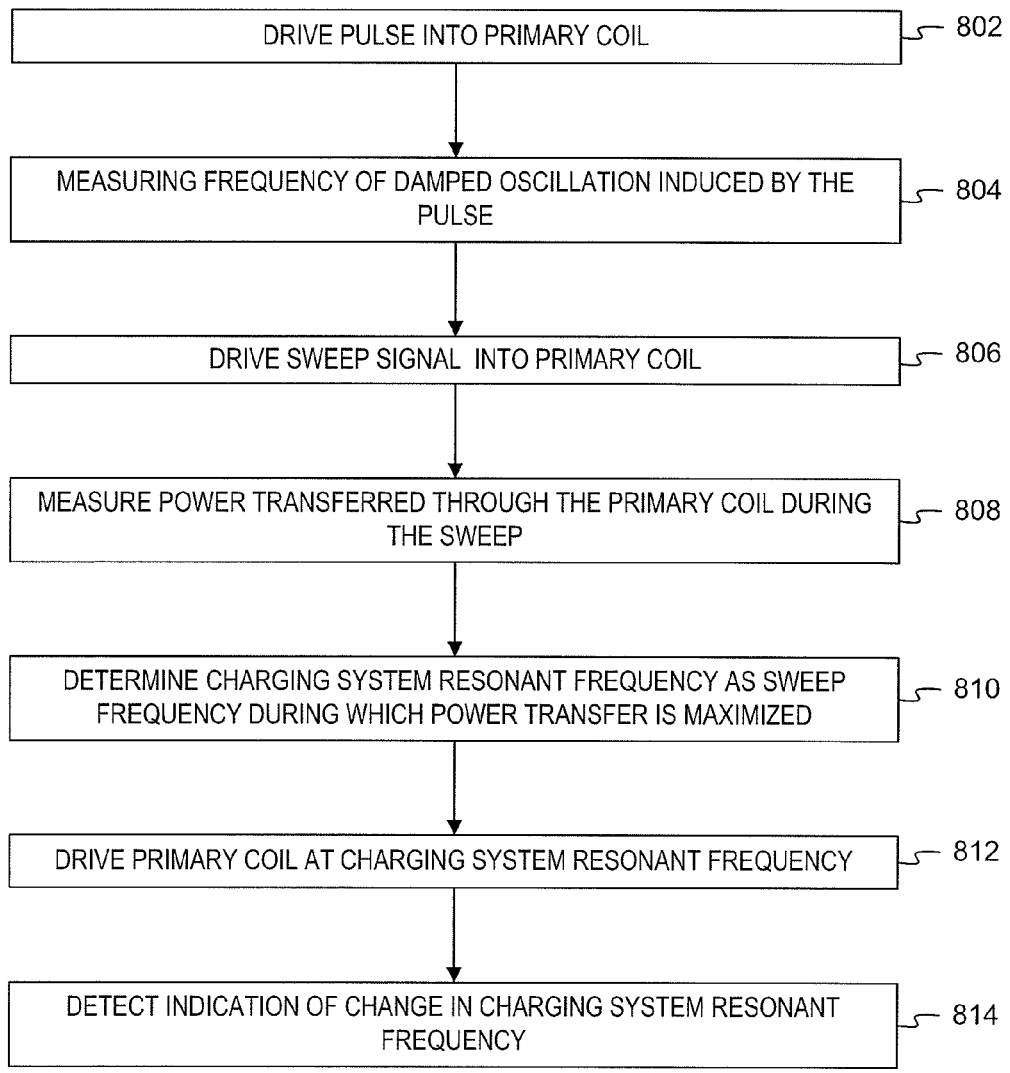

FIG. 8 shows a flow diagram of an illustrative method for charging the rechargeable power cell 210 in the IMD 110 based on a charging system resonant frequency estimate made in an external charging device 155 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 8, as well as other operations described herein, can be implemented as instructions stored in a computer readable medium and executed by a processor.

In block 802, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 causes the signal generator 226 to drive a pulse or a step signal into the inductor 290. The pulse induces oscillation in the inductor 290.

In block 804, the resonant frequency measurement unit 288 determines the frequency of the oscillation. The frequency of the oscillation is at or near the resonant frequency of the charging system. Any suitable frequency measurement technique, such as Fourier analysis or cycle time measurement may be used to determine the fundamental frequency of the oscillation. The resonant frequency measurement unit 288 uses the measured frequency of the oscillation as an initial estimate of the charging system resonant frequency.

In block 806, the recharge controller 280 of the external charging device 155 programs (or otherwise directs) the function/sweep generator 282 to drive a sweep signal into the inductor 290. The start frequency of the sweep signal is based on the initial resonant frequency estimate derived from the preceding pulse and oscillation frequency measurement. Because the initial resonant frequency estimate may be relatively close to the actual charging system resonant frequency, the sweep signal may be programmed to encompass a narrow range of frequencies (e.g., 100 Hz or less) about the initial resonant frequency estimate.

In block 808, as the sweep signal is driven into the inductor 290, the resonant frequency measurement unit 288 measures the power transferred through the inductor 290.

In block 810, the resonant frequency measurement unit 288 determines the resonant frequency of the charging system based on measurements of power transferred through the inductor 290 during the sweep. The frequency of the sweep at which power transfer is maximized may be deemed the charging system resonant frequency.

In block 812, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 814, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 9:
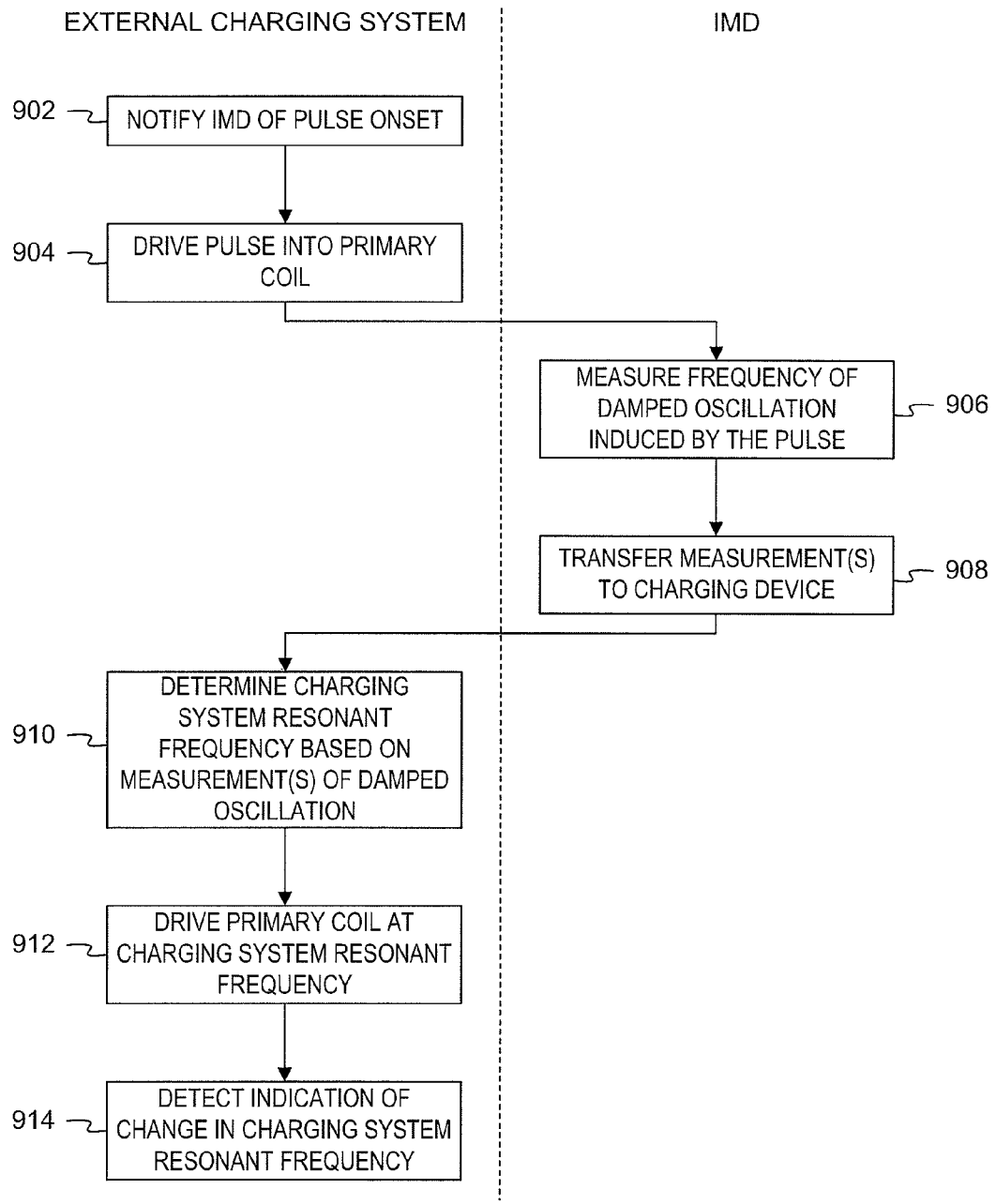

FIG. 9 shows a flow diagram of an illustrative method for charging the rechargeable power cell 210 in the IMD 110 based on a charging system resonant frequency estimate made cooperatively by an external charging device 155 and an IMD 110 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 9, as well as other operations described herein, can be implemented as instructions stored in a computer readable medium and executed by a processor.

In block 902, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 notifies the IMD 110 of a pulse to be imminently driven into the inductor 290. The notification causes the IMD 110 to prepare to gather measurements indicative of the frequency of oscillation induced by the pulse.

In block 904, the pulse generator 284 of the signal generator 226 drives a pulse or a step signal into the inductor 290. The pulse induces oscillation in the inductor 290.

In block 906, the resonant frequency measurement unit 224 of the IMD 110 performs measurements with regard to the oscillation. The resonant frequency measurement unit 224 may measure the frequency of the oscillation or gather information (e.g., cycle timing, waveform samples, etc.) that can be used by the charging device 155 to determine the frequency of the oscillation. Any suitable frequency measurement technique, such as Fourier analysis or cycle time measurement may be used to determine the fundamental frequency of the oscillation.

In block 908, the IMD transfers the gathered measurements of the oscillation to the external charging device 155.

In block 910, the external charging device 155 estimates the resonant frequency of the charging system based on the frequency of the oscillation. The frequency of the oscillation is at or near the resonant frequency of the charging system.

In block 912, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 914, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 10:
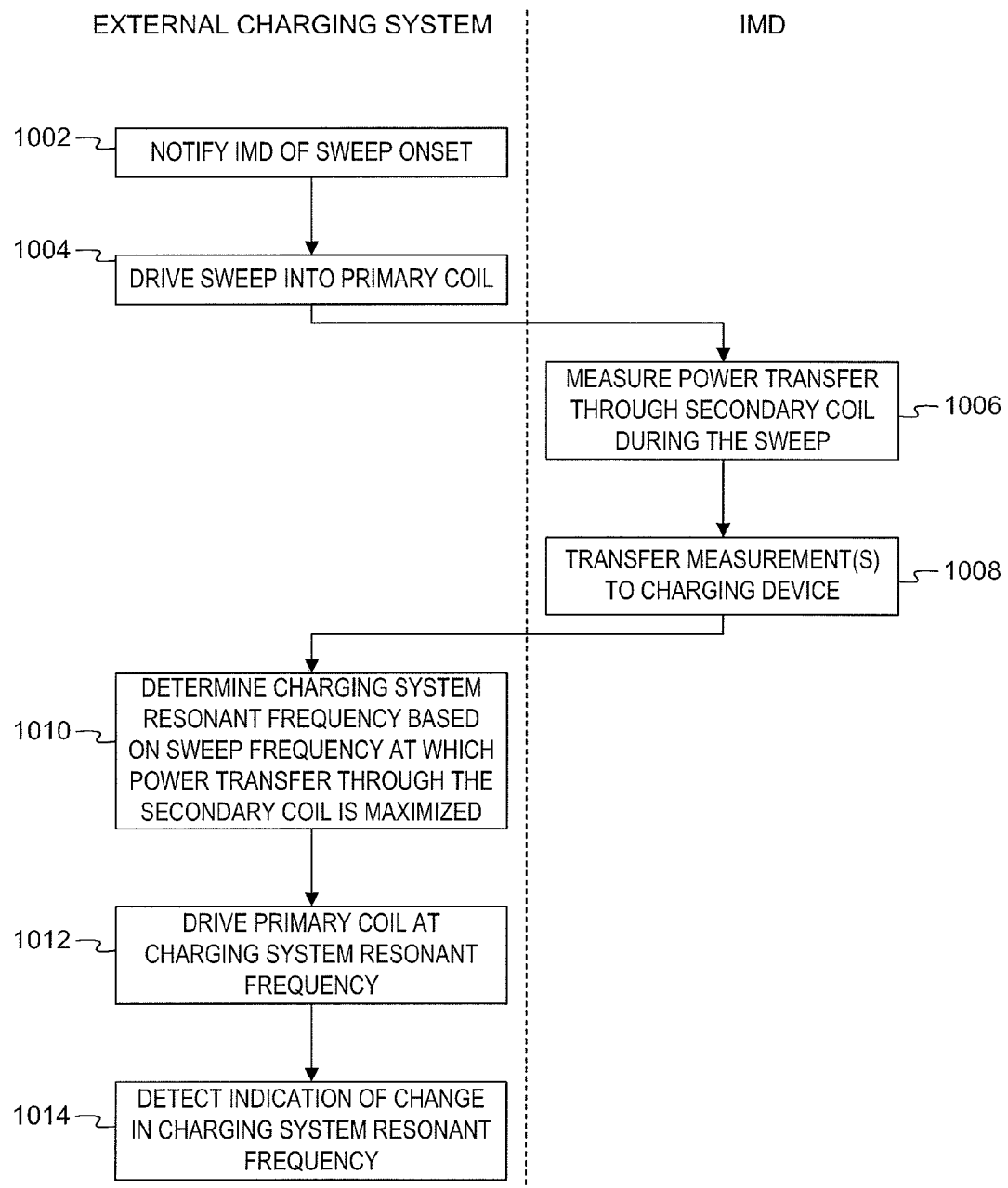

FIG. 10 shows a flow diagram of an illustrative method for charging the rechargeable power cell 210 in the IMD 110 based on a charging system resonant frequency estimate made cooperatively by an external charging device 155 and an IMD 110 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 10, as well as other operations described herein, can be implemented as instructions stored in a computer readable medium and executed by a processor.

In block 1002, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 notifies the IMD 110 of an upcoming sweep signal to be driven into the inductor 290. The notification causing the IMD 110 to prepare to gather measurements indicative of the sweep frequency at which power transfer from the charging device 155 to the IMD 110 is maximized.

In block 1004, the function/sweep generator 282 of the signal generator 226 drives a sweep signal into the inductor 290. The start frequency and frequency range of the sweep signal can vary, but are intended to encompass the expected variation in the resonant frequency of the charging system (e.g., 8-13 KHz).

In block 1006, the energy transferred from the external charging device 155 to the IMD 110 is monitored by the resonant frequency measurement unit 224 of the IMD 110 as the sweep signal is driven into the inductor 290. Energy transfer may be monitored by a power measurement circuit associated with the resonant frequency measurement unit 224.

In block 1008, any information indicative of the resonant frequency (e.g., a frequency value, time value, power measurements, etc.) gathered by the IMD 110 is transferred to the external charging device 115 via the communication units 260, 250.

In block 910, the external charging device determines the charging system resonant frequency based on the information indicative of frequency of maximal energy transfer provided by the IMD 110. The charging system resonant frequency may be deemed to be the frequency of the sweep signal during which energy transfer to the IMD 110 is maximized.

In block 1012, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 1014, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 11:
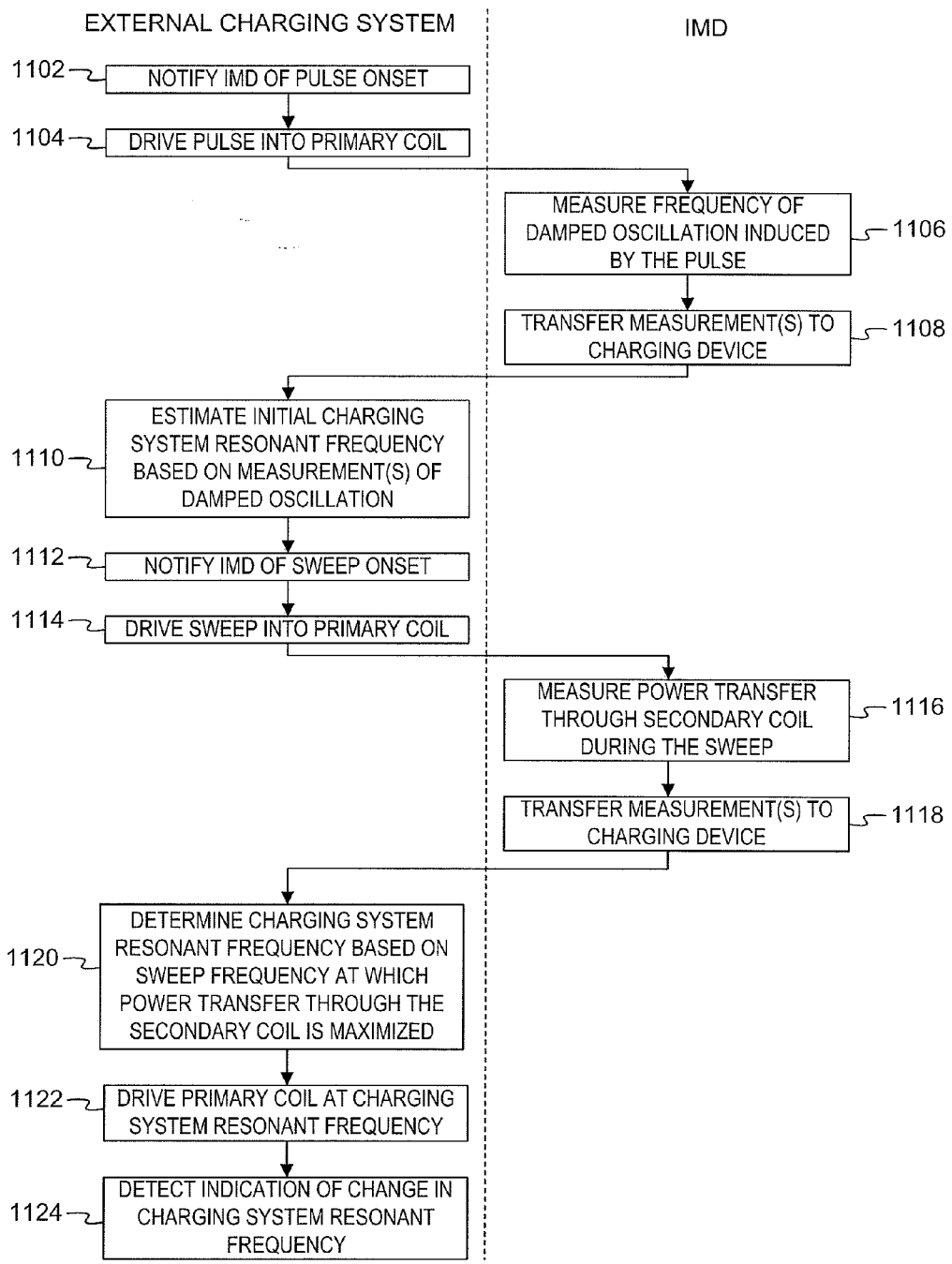

FIG. 11 shows a flow diagram of an illustrative method for charging the rechargeable power cell 210 in the IMD 110 based on a charging system resonant frequency estimate made cooperatively by an external charging device 155 and an IMD 110 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 11, as well as other operations described herein, can be implemented as instructions stored in a computer readable medium and executed by a processor.

In block 1102, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 notifies the IMD 110 of a pulse to be imminently driven into the inductor 290. The notification causes the IMD 110 to prepare to gather measurements indicative of the frequency of oscillation induced by the pulse.

In block 1104, the pulse generator 284 of the signal generator 226 drives a pulse or a step signal into the inductor 290. The pulse induces oscillation in the inductor 290.

In block 1106, the resonant frequency measurement unit 224 of the IMD 110 performs measurements with regard to the oscillation. The resonant frequency measurement unit 224 may measure the frequency of the oscillation or gather information (e.g., cycle timing, waveform samples, etc.) that can be used by the charging device 155 to determine the frequency of the oscillation. Any suitable frequency measurement technique, such as Fourier analysis or cycle time measurement may be used to determine the fundamental frequency of the oscillation.

In block 1108, the IMD transfers the gathered measurements of the oscillation to the external charging device 155.

In block 1110, the external charging device 155 derives an initial estimate of the resonant frequency of the charging system from the frequency of the oscillation. The frequency of the oscillation may be near or at the resonant frequency of the charging system.

In block 1112, the recharge controller 280 of the external charging device 155 notifies the IMD 110 of an upcoming sweep signal to be driven into the inductor 290. The notification causing the IMD 110 to prepare to gather measurements indicative of the sweep frequency at which power transfer from the charging device 155 to the IMD 110 is maximized.

In block 1114, the function/sweep generator 282 of the signal generator 226 drives a sweep signal into the inductor 290. The start frequency and frequency range of the sweep signal are based on the initial resonant frequency estimate derived from the preceding pulse and oscillation frequency measurement. Because the initial resonant frequency estimate may be relatively close to the actual charging system resonant frequency, the sweep signal may be programmed to encompass a narrow range of frequencies (e.g., 100 Hz or less) about the initial resonant frequency estimate.

In block 1116, the energy transferred from the external charging device 155 to the IMD 110 is monitored by the resonant frequency measurement unit 224 of the IMD 110 as the sweep signal is driven into the inductor 290. Energy transfer may be monitored by a power measurement circuit associated with the resonant frequency measurement unit 224.

In block 1118, any information indicative of the resonant frequency (e.g., a frequency value, time value, power measurements, etc.) gathered by the IMD 110 is transferred to the external charging device 115 via the communication units 260, 250.

In block 1120, the external charging device 155 determines the charging system resonant frequency based on the information indicative of frequency of maximal energy transfer provided by the IMD 110. The charging system resonant frequency may be deemed to be the frequency of the sweep signal during which energy transfer to the IMD 110 is maximized.

In block 1122, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 1124, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 12:
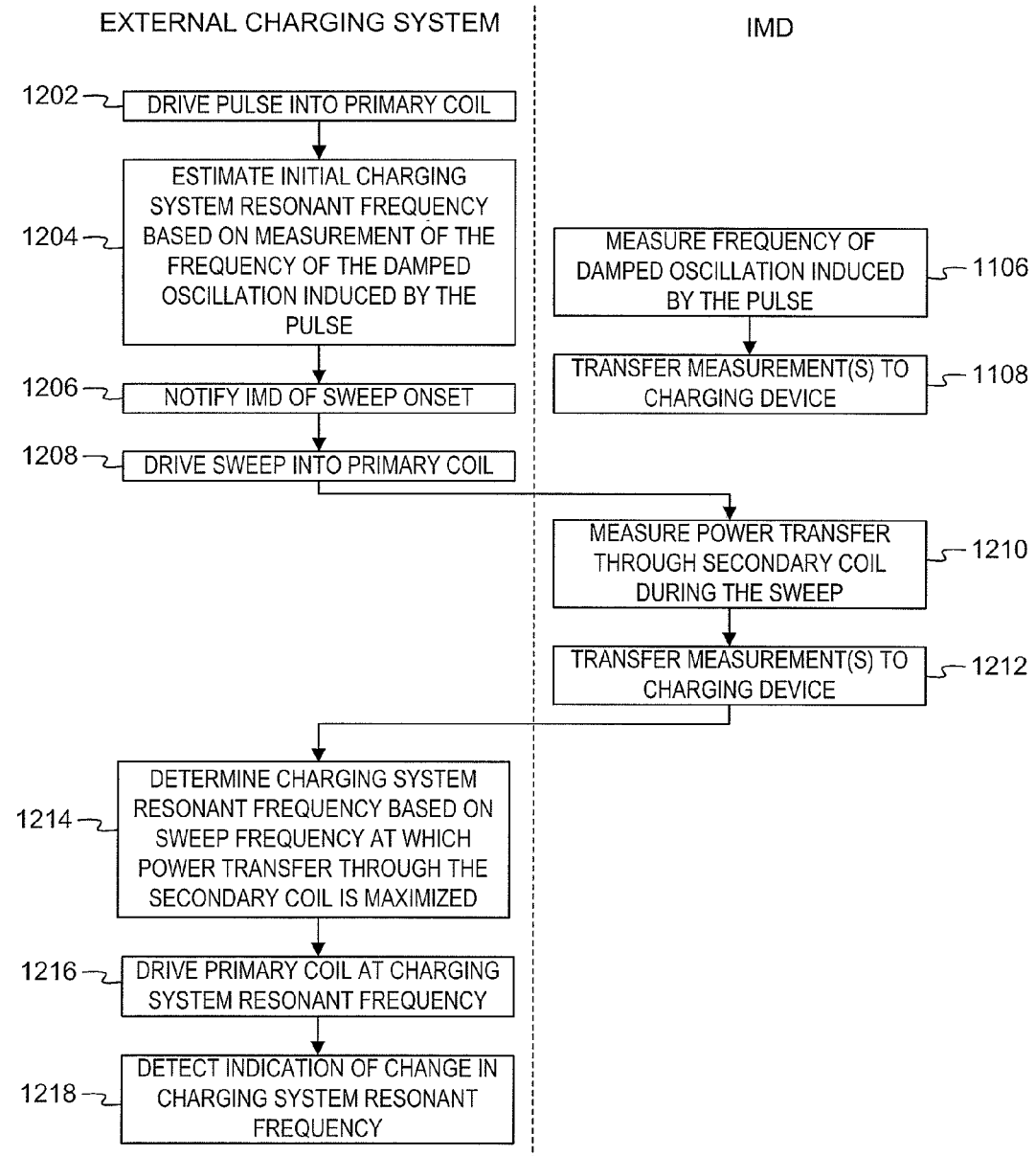

FIG. 12 shows a flow diagram of an illustrative method for charging the rechargeable power cell 210 in the IMD 110 based on a charging system resonant frequency estimate made cooperatively by an external charging device 155 and an IMD 110 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 12, as well as other operations described herein, can be implemented as instructions stored in a computer readable medium and executed by a processor.

In block 1202, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 causes the signal generator 226 to drive a pulse or a step signal into the inductor 290. The pulse induces oscillation in the inductor 290.

In block 1204, the resonant frequency measurement unit 288 gathers measurements indicative of the frequency of the oscillation and derives an initial estimate of the resonant frequency of the charging system from the measurements. Any suitable frequency measurement technique, such as Fourier analysis or cycle time measurement may be used to determine the fundamental frequency of the oscillation.

In block 1206, the recharge controller 280 of the external charging device 155 notifies the IMD 110 of an upcoming sweep signal to be driven into the inductor 290. The notification causing the IMD 110 to prepare to gather measurements indicative of the sweep frequency at which power transfer from the charging device 155 to the IMD 110 is maximized.

In block 1208, the function/sweep generator 282 of the signal generator 226 drives a sweep signal into the inductor 290. The start frequency and frequency range of the sweep signal are based on the initial resonant frequency estimate derived from the preceding pulse and oscillation frequency measurement. Because the initial resonant frequency estimate may be relatively close to the actual charging system resonant frequency, the sweep signal may be programmed to encompass a narrow range of frequencies (e.g., 100 Hz or less) about the initial resonant frequency estimate.

In block 1210, the energy transferred from the external charging device 155 to the IMD 110 is monitored by the resonant frequency measurement unit 224 of the IMD 110 as the sweep signal is driven into the inductor 290. Energy transfer may be monitored by a power measurement circuit associated with the resonant frequency measurement unit 224.

In block 1212, any information indicative of the resonant frequency (e.g., a frequency value, time value, power measurements, etc.) gathered by the IMD 110 is transferred to the external charging device 115 via the communication units 260, 250.

In block 1214, the external charging device 155 determines the charging system resonant frequency based on the information indicative of frequency of maximal energy transfer provided by the IMD 110. The charging system resonant frequency may be deemed to be the frequency of the sweep signal during which energy transfer to the IMD 110 is maximized.

In block 1216, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 1218, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

Figure 13:
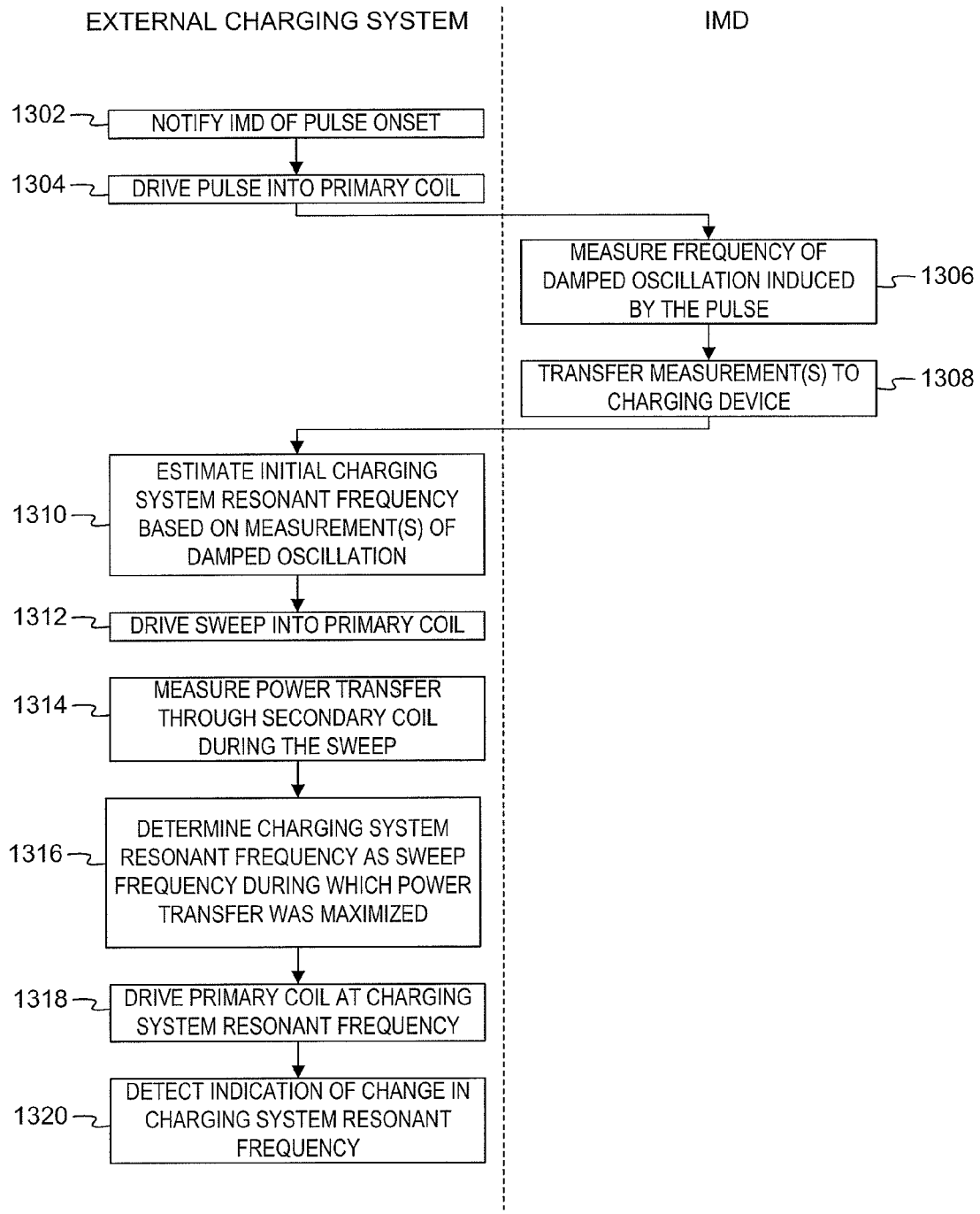

FIG. 13 shows a flow diagram of an illustrative method for charging the rechargeable power cell 210 in the IMD 110 based on a charging system resonant frequency estimate made cooperatively by an external charging device 155 and an IMD 110 in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of FIG. 13, as well as other operations described herein, can be implemented as instructions stored in a computer readable medium and executed by a processor.

In block 1302, the IMD 110 and the external charging device 155 are positioned to enable communication and charging of the rechargeable power cell 210. In order to optimize transcutaneous energy transfer, the external charging device 155 initiates measurement of the charging system resonant frequency, where the charging system includes the inductors 290 and 205 and various other components. The recharge controller 280 of the external charging device 155 notifies the IMD 110 of a pulse to be imminently driven into the inductor 290. The notification causes the IMD 110 to prepare to gather measurements indicative of the frequency of oscillation induced by the pulse.

In block 1304, the pulse generator 284 of the signal generator 226 drives a pulse or a step signal into the inductor 290. The pulse induces oscillation in the inductor 290.

In block 1306, the resonant frequency measurement unit 224 of the IMD 110 performs measurements with regard to the oscillation. The resonant frequency measurement unit 224 may measure the frequency of the oscillation or gather information (e.g., cycle timing, waveform samples, etc.) that can be used by the charging device 155 to determine the frequency of the oscillation. Any suitable frequency measurement technique, such as Fourier analysis or cycle time measurement may be used to determine the fundamental frequency of the oscillation.

In block 1308, the IMD transfers the gathered measurements of the oscillation to the external charging device 155 via the communication units 260, 250.

In block 1310, the external charging device 155 derives an initial estimate of the resonant frequency of the charging system from the frequency of the oscillation as determined based on the information provided by the IMD 110. The frequency of the oscillation may be near or at the resonant frequency of the charging system.

In block 1312, the recharge controller 280 of the external charging device 155 programs (or otherwise directs) the function/sweep generator 282 to drive a sweep signal into the inductor 290. The start frequency of the sweep signal is based on the initial resonant frequency estimate derived from the preceding pulse and oscillation frequency measurement. Because the initial resonant frequency estimate may be relatively close to the actual charging system resonant frequency, the sweep signal may be programmed to encompass a narrow range of frequencies (e.g., 100 Hz or less) about the initial resonant frequency estimate.

In block 1314, as the sweep signal is driven into the inductor 290, the resonant frequency measurement unit 288 of the external charging device 155 measures the power transferred through the inductor 290.

In block 1316, the resonant frequency measurement unit 288 determines the resonant frequency of the charging system based on measurements of power transferred through the inductor 290 during the sweep. The frequency of the sweep at which power transfer is maximized may be deemed the charging system resonant frequency.

In block 1318, the recharge controller 280 of the external charging device 155 programs (or otherwise directs) the function/sweep generator 282 to provide a drive signal set to the determined charging system resonant frequency into the inductor 290, thereby optimizing transfer of charging energy from the external charging device 155 to the IMD 110.

In block 1320, the external charging device 155 and/or the IMD 110 monitor for indications of a change in the charging system resonant frequency. For example, detected motion of the external charging device 155 or an unexpected reduction in transcutaneous energy transfer may be indicative of a change in charging system resonant frequency. If a change in resonant frequency is indicated, the external charging device 155 may initiate resonant frequency measurement and correction in accordance with the operations explained above.

The above discussion is meant to be illustrative of the principles and various embodiments of the present invention. Numerous variations and modifications will become apparent to those skilled in the art once the above disclosure is fully appreciated. For example, while embodiments of the present disclosure have been described with reference to a vagus nerve stimulator, those skilled in the art will understand that embodiments are applicable to any IMD or device using a rechargeable power cell. It is intended that the following claims be interpreted to embrace all such variations and modifications.

What is claimed is:

1. A method for charging a power cell in an implantable medical device (IMD), comprising:
    providing an electrical pulse to an inductor external to the IMD;
    measuring a first frequency of an oscillation signal induced in the inductor by the electrical pulse; and
    driving the inductor with a drive signal operative to induce a current in the IMD, the induced current operative to charge the power cell of the IMD, the drive signal having a second frequency based on the measured first frequency of the oscillation signal.

2. The method of claim 1, wherein the electrical pulse further comprises a rise time or a fall time operative to induce the oscillation signal.

3. The method of claim 1, wherein the measuring comprises determining the first frequency of the oscillation signal in a recharging device external to the IMD.

4. The method of claim 1, wherein the measuring comprises determining the first frequency of the oscillation signal based on Fourier analysis.

5. The method of claim 1, wherein the measuring comprises determining a time interval between any peak, valley, or zero crossing of the oscillation signal.

6. The method of claim 1, further comprising:
    driving the inductor with a sweep signal of changing frequency, wherein the range of the changing frequency is based on the measured first frequency of the oscillation signal; and
    determining a third frequency of the sweep signal at a time of maximum power transfer between the inductor and the IMD.

7. The method of claim 6, wherein the sweep signal comprises a signal swept about the measured first frequency of the oscillation signal.

8. The method of claim 6, wherein the determining comprises:
measuring power transfer between the inductor and the IMD using a measurement circuit in the IMD; and
communicating an indication of the third frequency to a recharging device external to the IMD.

9. The method of claim 1, wherein the electrical pulse is periodic.

10. The method of claim 1, further comprising:
detecting an indication that a resonant frequency of a charging system has changed; and
adjusting the drive signal based on the detected indication.

11. The method of claim 10, wherein detecting the indication further comprises detecting motion of the inductor external to the IMD.

12. The method of claim 1, wherein the oscillating signal has a frequency between 8 and 13 kilohertz.

13. A system for charging a rechargeable power cell in an implantable medical device (IMD), comprising:
a recharging device external to the IMD, the recharging device comprising:
a primary coil configured to generate a magnetic field operative to induce flow of recharging current in the IMD;
a pulse generator configured to drive a pulse into the primary coil operative to induce an oscillation signal in the primary coil;
a signal generator configured to drive a drive signal across the primary coil at a first frequency based on a second frequency of the oscillation signal; and
a frequency measurement system configured to measure the second frequency of the oscillation signal.

14. The system of claim 13, wherein the frequency measurement system applies Fourier analysis to determine the second frequency of the oscillation signal.

15. The system of claim 13, wherein the frequency measurement system determines a time interval between any peak, valley, or zero crossing of the oscillation signal.

16. The system of claim 13, wherein the signal generator is configured to drive the primary coil with a sweep signal, and a start frequency and an end frequency of the sweep signal are based on the measured second frequency of the oscillation signal.

17. The system of claim 16, further comprising a power meter within one of the recharging device and the IMD, the power meter configured to measure power transferred from the primary coil to the IMD, and to determine a third frequency of the sweep signal at which maximum power transfer occurs.

18. The system of claim 17, wherein the IMD comprises:
a secondary coil, wherein the power meter is configured to measure power transferred through the secondary coil, and
a communication unit configured to communicate, to the recharging device, information indicative of the third frequency.

19. The system of claim 13, wherein the recharging device comprises a motion detector, and the pulse generator is configured to drive a pulse into the primary coil based on the motion detector detecting movement of the recharging device.

20. A charger for transcutaneously recharging an implanted power cell, comprising:
a primary coil configured to generate a magnetic field that induces flow of recharging current in a secondary coil of an implanted medical device (IMD);
a signal generator configured to:
drive a pulse into the primary coil operative to induce an oscillation signal in the primary coil;
drive a drive signal into the primary coil, a first frequency of the drive signal based on a second frequency of the oscillation signal; and to
drive a sweep signal across the primary coil, a start frequency and an end frequency of the sweep signal based on the second frequency of the oscillation signal.

21. The charger of claim 20, wherein the signal generator is configured to intermittently drive the pulse.

22. The charger of claim 20, further comprising a frequency determination circuit configured to determine the second frequency of the oscillation signal.

23. The charger of claim 20, further comprising a communication unit configured to wirelessly communicate with the IMD, and to receive from the IMD information indicative of a third frequency of the sweep signal at which maximum power is transferred through the secondary coil.

24. The charger of claim 23, wherein the signal generator is configured to drive the drive signal at approximately the third frequency.

25. The charger of claim 20, further comprising a motion detection circuit configured to detect one of motion of the charger relative to the IMD and motion of the charger, and wherein the signal generator is configured to drive a pulse based on the detected motion of the charger.

* * * * *